(12) United States Patent
Takahashi

(10) Patent No.: US 9,183,621 B2
(45) Date of Patent: Nov. 10, 2015

(54) IMAGE PROCESSING APPARATUS AND RADIOGRAPHIC APPARATUS HAVING THE SAME

(75) Inventor: Wataru Takahashi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 61 days.

(21) Appl. No.: 14/343,356

(22) PCT Filed: Aug. 21, 2012

(86) PCT No.: PCT/JP2012/005237
§ 371 (c)(1),
(2), (4) Date: Jun. 23, 2014

(87) PCT Pub. No.: WO2013/035255
PCT Pub. Date: Mar. 14, 2013

(65) Prior Publication Data
US 2014/0314333 A1      Oct. 23, 2014

(30) Foreign Application Priority Data
Sep. 7, 2011   (JP) ................................. 2011-195186

(51) Int. Cl.
| | | |
|---|---|---|
| G06K 9/40 | (2006.01) | |
| G06T 5/10 | (2006.01) | |
| G06T 5/00 | (2006.01) | |
| A61B 6/00 | (2006.01) | |

(52) U.S. Cl.
CPC ................. *G06T 5/10* (2013.01); *A61B 6/5258* (2013.01); *G06T 5/002* (2013.01); *A61B 6/4233* (2013.01); *A61B 6/4452* (2013.01); *A61B 6/505* (2013.01); *A61B 6/542* (2013.01); *G06T 2207/10116* (2013.01); *G06T 2207/10121* (2013.01); *G06T2207/20016* (2013.01); *G06T 2207/20192* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 7,072,525 B1 * | 7/2006 | Covell | 382/261 |
| 2002/0071600 A1 * | 6/2002 | Yamada | 382/132 |
| 2004/0258325 A1 * | 12/2004 | Sasada | 382/275 |

(Continued)

FOREIGN PATENT DOCUMENTS

| | | |
|---|---|---|
| JP | 2002-133410 A | 5/2002 |
| JP | 2004-242285 A | 8/2004 |

(Continued)

OTHER PUBLICATIONS

International Search Report issued in International Application No. PCT/JP2012/005237 issued on Dec. 4, 2012.

*Primary Examiner* — Sean Motsinger
(74) *Attorney, Agent, or Firm* — McDermott Will & Emery LLP

(57) ABSTRACT

Provision can be made of a high-speed image processing apparatus that eliminates poor visibility in a dotted configuration or a superimposed portion of two streaks upon removing a false image due to statistical noise. That is, provision can be made of a high-speed image processing apparatus capable of outputting a processed image of high visibility in accordance with a shape of a configuration of a subject appearing in an original image upon removing a false image associated with the statistical noise. A band image noise extract generating unit performs image processing by superimposing a band image, an isotropic blur image, and an anisotropic blur image while changing weighting for each pixel in accordance with edge reliability. Such a construction eliminates poor visibility in the dotted configuration or the superimposed portion of two streaks upon removing the false image in the original image.

16 Claims, 13 Drawing Sheets

(56) References Cited

U.S. PATENT DOCUMENTS

2005/0089242 A1    4/2005  Shinbata
2006/0020203 A1*   1/2006  Tamura ........................ 600/437
2010/0142790 A1*   6/2010  Chang ......................... 382/132

FOREIGN PATENT DOCUMENTS

JP    4072491 B2    4/2008
JP    4197392 B2   12/2008

* cited by examiner

Fig.6
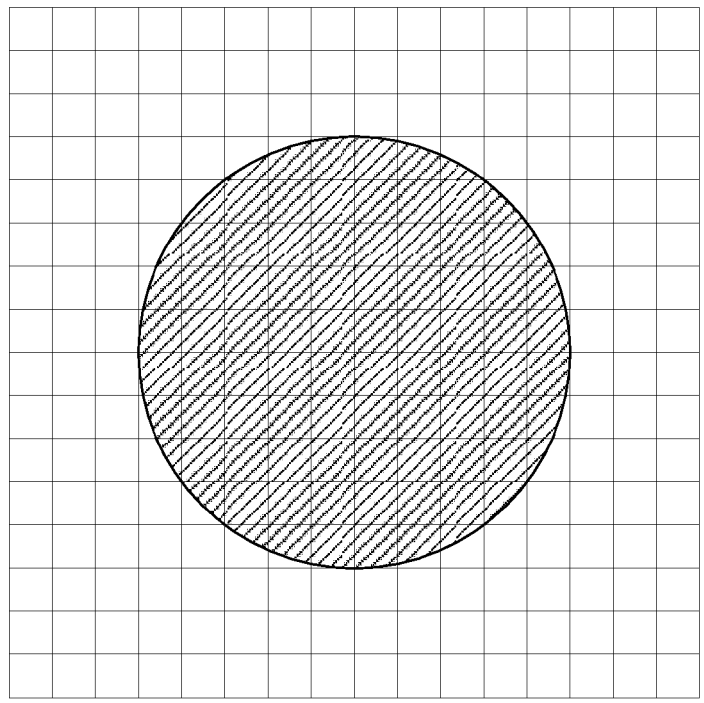
BAND IMAGE
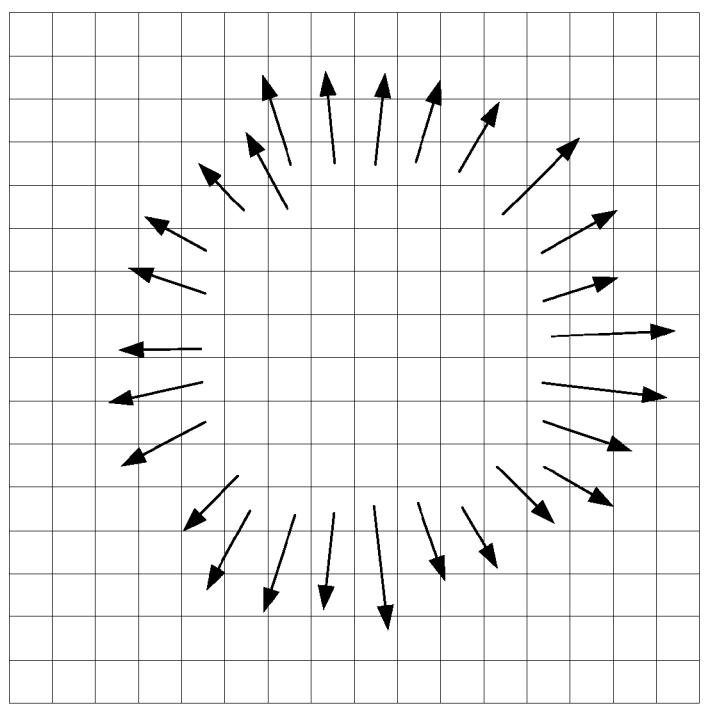
GRADIENT

Fig.7
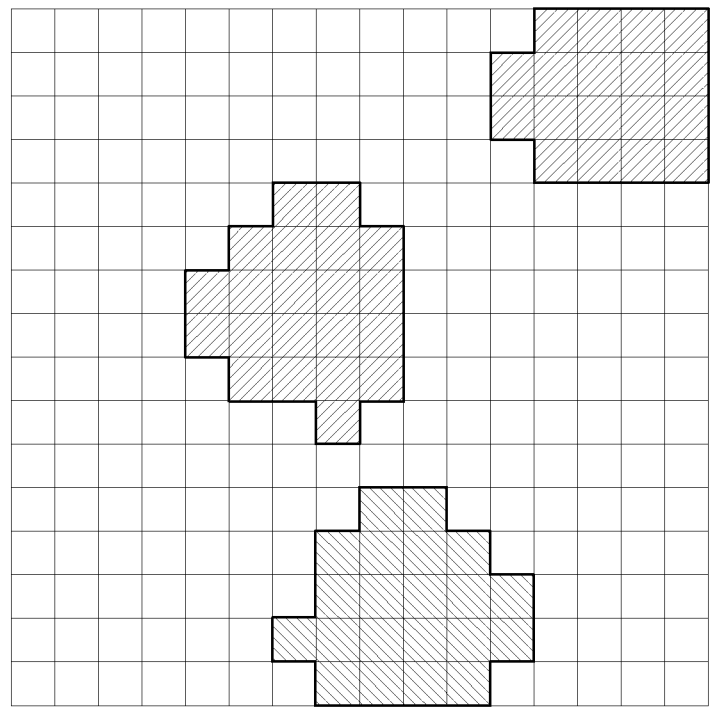
BAND IMAGE
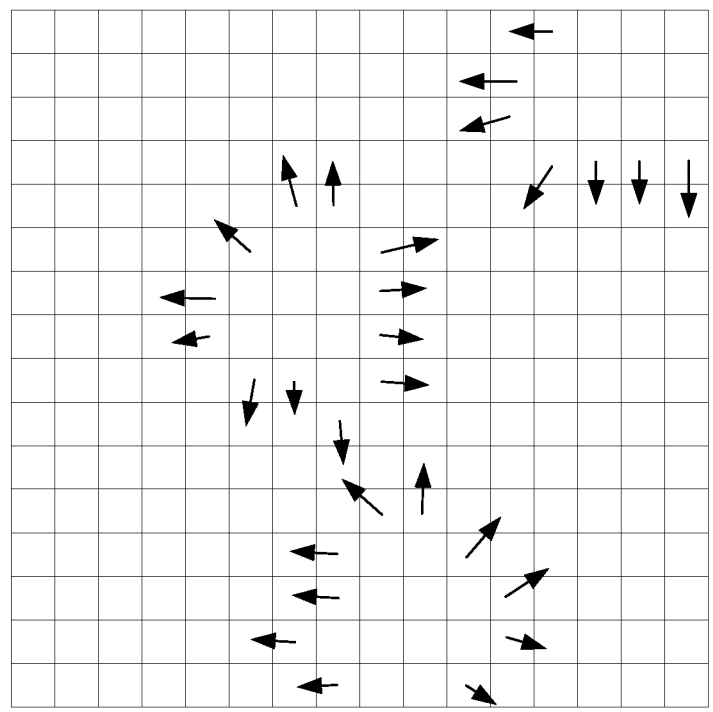
GRADIENT

Fig.14
THREE-DIMENSIONAL VIEW
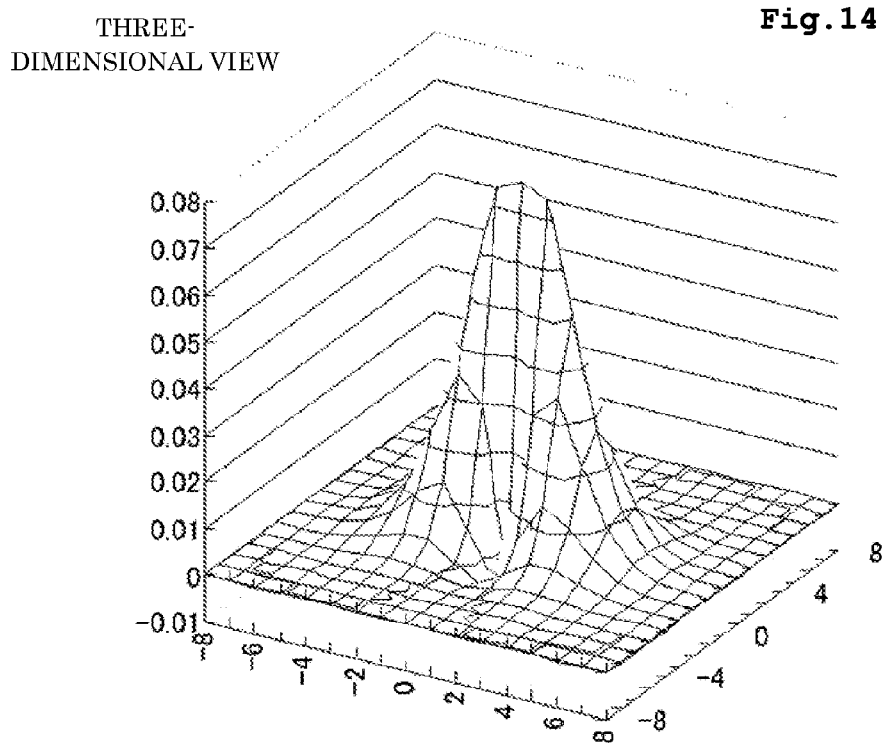
PLAN VIEW
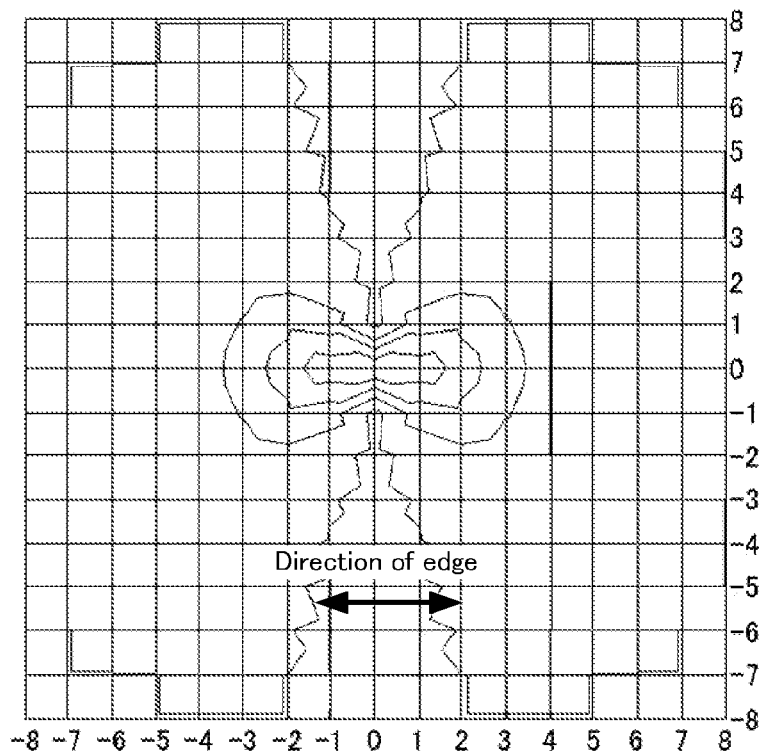

Fig.15
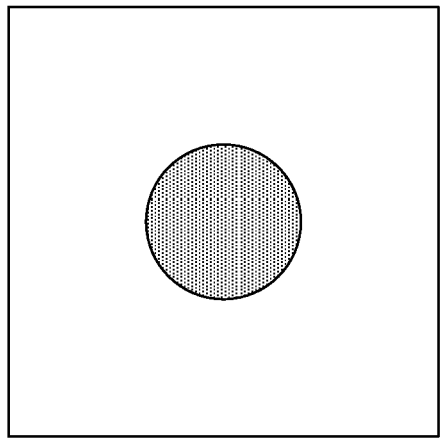
Fig.16
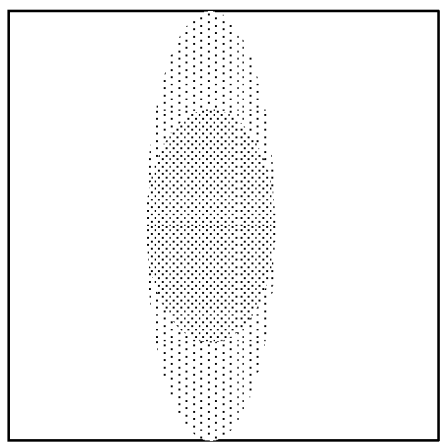 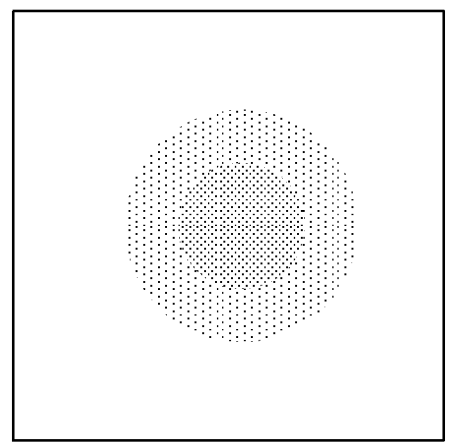
Fig.17
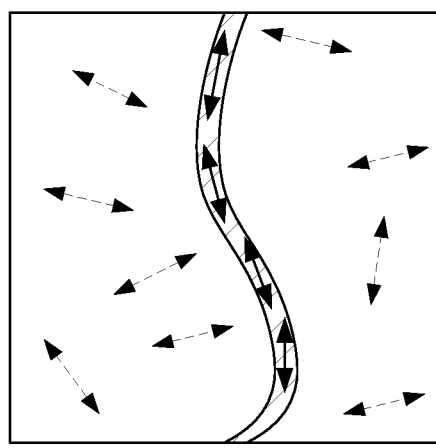 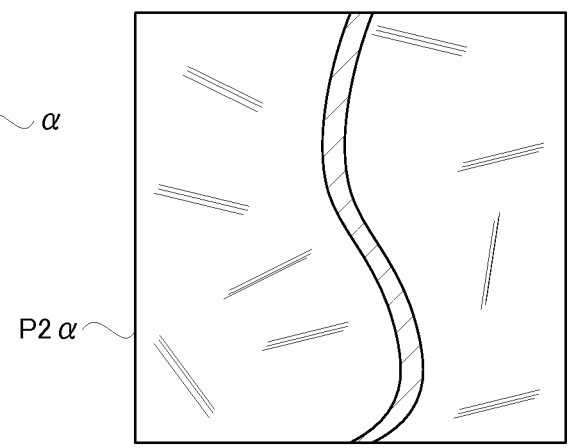

Fig.20
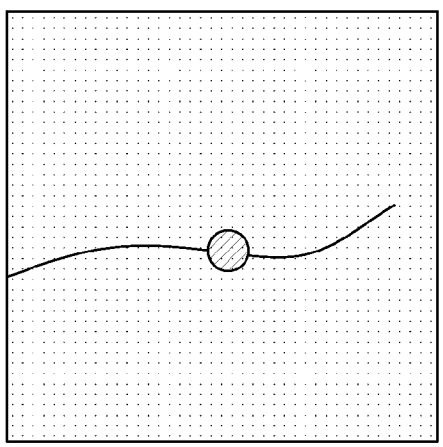 Prior art
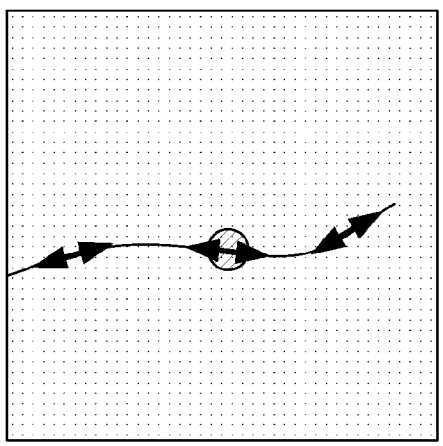
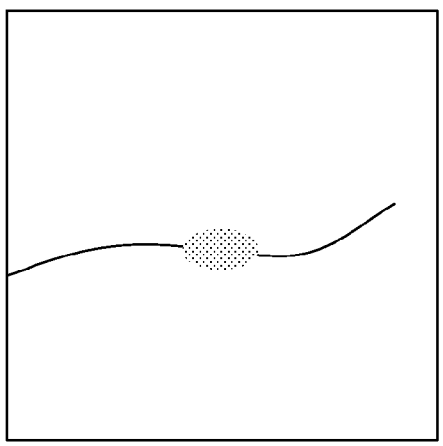

Fig.21
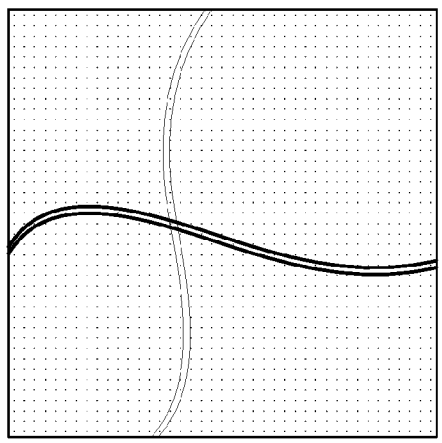 Prior art
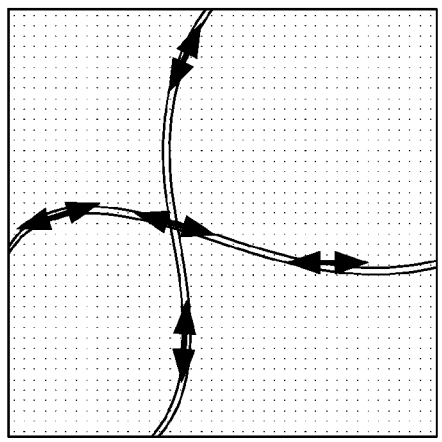
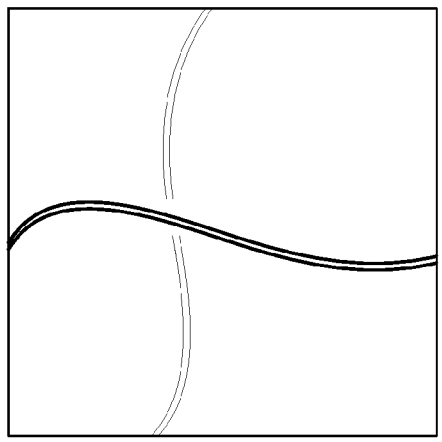

IMAGE PROCESSING APPARATUS AND RADIOGRAPHIC APPARATUS HAVING THE SAME

RELATED APPLICATIONS

This application is the U.S. National Phase under 35 U.S.C. §371 of International Application No. PCT/JP2012/005237, filed on Aug. 21, 2012, which in turn claims the benefit of Japanese Application No. 2011-195186, filed on Sep. 7, 2011, the disclosures of which Applications are incorporated by reference herein.

TECHNICAL FIELD

The present invention relates to an image processing apparatus and a radiographic apparatus having the image processing apparatus, the image processing apparatus allowing removal of statistical noise in an image upon radiography.

BACKGROUND ART

A medical institution is equipped with a radiographic apparatus configured to obtain a subject image with radiation. Such a radiographic apparatus suppresses a dose of radiation to be emitted to the extent possible upon radiography. This is because radiation exposure unnecessary for a subject has to be avoided.

Accordingly, a granular false image referred to as statistical noise likely appears in the obtained image. The statistical noise is, for example, derived from unevenness of radiation detection by each detecting element of a radiation detector, and tends to be more remarkable with a less dose of radiation. Consequently, the false image remarkably appears in a portion of the image, such as a bone, where a dose of radiation is likely to lack.

The statistical noise appears not only in the bone portion but also the entire image. Thus, a construction has been conventionally designed that removes the false image derived from the statistical noise from the image to enhance visibility of the image. See, for example, Japanese Patent No. 4072491 and Japanese Patent Publication 2004-242285A. Such the image processing has a problem how an original subject image is allowed to remain while the false image is removed.

Hereinunder described are two sophisticated examples of the image processing with the conventional construction. With a method in Japanese Patent No. 4197392, edge reliability is firstly calculated for each pixel. The edge reliability is an index representing whether a variation in pixel value between a pixel constituting the image and a pixel surrounding the pixel is derived from a configuration of the subject or from the statistical noise. Then, different weights are applied to each of the pixels in accordance with the calculation results to perform image processing. Specifically, a weight of an anisotropic filter image is increased for a pixel with high edge reliability and pixel values variation due to the configuration of the subject, the anisotropic filter image being obtained by applying an anisotropic filter to an image to perform smoothing depending on a direction. On the other hand, a weight of a band image is increased for a pixel with low edge reliability and pixel values variation due to the statistical noise. This allows removal of the false image derived from the statistical noise in the image while the configuration of the subject remains.

Here, an edge indicated by the edge reliability is a streak figure derived from the configuration of the subject. Since the false image derived from the statistical noise is granular, the false image has no streak appearing therein. Accordingly, a streak figure in the image does not represent the statistical noise but represents the configuration of the subject. Thus, the streak configuration derived from the subject appears in a portion of the image having high edge reliability. As a result, an anisotropic filter is applied to the streak configuration.

In this case, the anisotropic filter is applied so as to smooth along the streak configuration. A direction of the anisotropic filter, i.e., a direction of the streak configuration is accurately calculated with suppressed noise influence by averaging gradient vectors adjacent to one another isotropically and correcting the vectors with a gradient vector with low resolution. This avoids blurring of the streak configuration itself while the statistical noise superimposed on the streak configuration is eliminated.

Next, description will be given of an image processing method in Patent Literature 4. In this method, an anisotropic filter is variable in accordance with the edge reliability even in the same direction. That is, an anisotropic filter with high direction dependency is applied when the edge reliability is high. This leads to image processing to the configuration in the image with remarkable streaks so as to remain the configuration, and leads to image processing to the blurred configuration in the image so as to remain the blurring.

| Patent Literature | |
|---|---|
| Patent Literature 1 | Japanese Patent No. 4072491 |
| Patent Literature 2 | Japanese Patent Publication No. 2004-242285A |
| Patent Literature 3 | Japanese Patent No. 4197392 |
| Patent Literature 4 | Japanese Patent Publication No. 2002-133410A |

SUMMARY OF INVENTION

Technical Problem

The conventional construction, however, has the following problem. Specifically, the conventional radiographic apparatus has a problem that a clear image is not obtainable through the image processing.

That is, with the construction of Japanese Patent No. 4197392, some part of the image has a deformed figure appearing therein. FIG. 20 illustrates a guide wire appearing in the image. The guide wire is inserted into a subject during operation. The guide wire is not a configuration derived from the subject. However, the guide wire is a streak object appearing in the image, and has to be visible for an operator. FIG. 20 illustrates in the upper side thereof an image prior to the image processing. Here, a guide wire is illustrated to have a thick part. The part is a balloon marker attached to the guide wire and indicating a position of a balloon for expanding a blood vessel.

FIG. 20 illustrates in the middle thereof image processing to the image in the upper side thereof. In the image, a part except for the guide wire has a low edge reliability, and thus weight of the band image increases. On the other hand, the part corresponding to the guide wire in the image has a high edge reliability, and thus weight of the anisotropic filter increases. This causes blurring of the part corresponding to the guide wire in the image in a direction of arrows as illustrated in the middle of FIG. 20.

At this time, the balloon marker of the guide wire is similarly blurred in the direction of the arrows. Accordingly, the balloon marker is drawn in the same direction as illustrated in the lower side of FIG. 20. In other words, the image processing causes an unnatural dot shape of the configuration, such as a balloon marker, in the image. Such a problem cannot be solved even when the direction of the guide wire is accurately calculated.

Moreover, a method in Japanese Patent Publication No. 2002-133410A includes a plurality of types of anisotropic filters in every direction. In addition, an anisotropic filter with low direction dependency is applied to a part in the image corresponding to a dot configuration, the part representing an intermediate value of noise reliability. Accordingly, drawing the dot configuration is suppressed. However, such the method is insufficient for obtaining the image most suitable for diagnosis.

Moreover, image processing causes poor visibility to a portion where two streaks superimpose, such as an intersection of blood vessels undergoing contrast radiography. FIG. 21 illustrates in the upper side thereof an image prior to undergoing image processing. The image has two types of thick-line and thin-line streaks intersecting each other. When the image processing in Japanese Patent No. 4197392 is performed to the image, an anisotropic filter is to be applied since the streaks in the image have high edge reliability. This causes blurred streaks in the image in the arrow direction, as illustrated in the middle of FIG. 21.

The direction of the thick-line streak is determined for the intersection of the streaks in accordance with the edge reliability. Consequently, applying the anisotropic filter causes an image as illustrated in the lower side of FIG. 21 in which the thin-line streak is divided by the thick-line streak. The intersection of the streaks should appear in the image with the two streaks being superimposed on each other. Thus, the image processing generates an unnatural intersection of the streaks.

On the other hand, the method of Japanese Patent Publication No. 2002-133410A includes a plurality of types of anisotropic filters for every direction. An anisotropic filter with low direction dependency is applied to the intersection of the streaks representing an intermediate value of the noise reliability. This suppresses division of the thick-line and thin-line streaks. However, such the method is insufficient for obtaining the image most suitable for diagnosis.

In addition, in the method of Japanese Patent Publication No. 2002-133410A, the plurality of anisotropic filters for every direction has to be held. This causes necessity of a large-scale memory device for storing them, leading to a problem especially when the memory device is incorporated into a hardware. Furthermore, it has been determined which anisotropic filter is to be used in accordance with a plurality of conditions, such as a direction and edge reliability, depending on a part of the image. This takes much time for the image processing, and especially causes a problem in real-time operation.

The present invention has been made regarding the state of the art noted above, and its one object is to provide a high-speed image processing apparatus and a radiographic apparatus having the image processing apparatus, the image processing apparatus eliminating poor visibility in a dotted configuration or a superimposed portion of two streaks upon removing a false image due to statistical noise.

Solution to Problem

The present invention adopts the following construction for overcoming the above drawback. One aspect of the present invention discloses an image processing apparatus for processing an image obtained by fluoroscopying a subject. The image processing apparatus includes (A) a band-image generating device configured to generate a band image by extracting a part of frequency components in an original image with a figure of the subject appearing therein; (B) a gradient calculating device configured to calculate magnitude and a direction of gradient of a pixel value for each pixel of the band image; (C) an isotropic blurring device configured to generate an isotropic blur image by applying an isotropic smoothing filter to the band image; (D) an anisotropic blurring device configured to generate an anisotropic blur image by applying an anisotropic smoothing filter to the band image, the anisotropic smoothing filter depending on the direction of the gradient; (E) an edge-reliability obtaining device configured to calculate an index for the each pixel in accordance with the magnitude of the gradient and pixel values surrounding the pixel in the band image; and (F) a processed image generating device configured to superimpose the band image, the isotropic blur image, and the anisotropic blur image for the each pixel with weighting based on the index, thereby generating a processed image with a noise component removed from the original image.

Operation and Effect

The aspect of the present invention allows provision of the image processing apparatus that eliminates poor visibility in a superimposed portion of two streaks upon removing a false image associated with the statistical noise. Specifically, the image processing apparatus according to the aspect of the present invention generates the isotropic blur image and the anisotropic blur image from the original image. The isotropic blur image is an image in which the false image is appropriately removed from a portion of the original image with no subject image appearing therein, whereas the anisotropic blur image is an image in which the false image is appropriately removed from a portion in the original image with the subject image appearing therein. Then, the processed image generating device superimposes the two images on the band image while performing weighting for each pixel, thereby generating a band image noise extract with a false image component removed from the band image. The band image noise extract is then used for removing the false image appearing in the original image.

Most characteristic in the present invention is that the processed image generating device performs image processing by superimposing the band image, the isotropic blur image, and the anisotropic blur image while changing weighting for each pixel in accordance with the edge reliability. Here, the edge reliability is an index for determining whether a variation in pixel value between a pixel to be processed and a pixel therearound depends on a subject figure or a false image. For instance, when the edge reliability has an intermediate value, it is determined that the pixel to be processed is located in a dotted figure in the band image or an intersection of two streak figures. With the aspect of the present invention, the band image noise extract is generated without using the anisotropic blur image for the dotted figure or the intersection (if using, with intensity lower than that of the isotropic blur image). A portion corresponding to the dotted figure in the anisotropic blur image is drawn in a given direction, whereby the figure in the portion is unnatural. On the other hand, a portion corresponding to the intersection is unnatural since the thick-line figure is extremely enhanced. With the aspect of the present invention, such the portions are not used upon generating the band image noise extract. Accordingly, the dotted configuration of the subject or the intersection where contours of the configuration superimpose in the finally-obtained processed image is not random, and thus holds visibility. As noted above, the processed image can be outputted having high visibility in accordance with a shape of the configuration of the subject appearing in the original image.

Moreover, with the aspect of the present invention, there is no need to hold a plurality of anisotropic filters for every direction as in the conventional construction, causing a downsized memory device for storing them. Furthermore, it may be determined which anisotropic filter is to be used only in accordance with the direction of the gradient depending on a portion of the image. This allows provision of the image processing apparatus with an enhanced processing speed.

Moreover, in the image processing apparatus according to the aspect of the present invention, an isotropic blurring device (c) applies an directionless isotropic smoothing filter, independent on isotropy, to the original image to generate an isotropic blur image, and an anisotropic blurring device (d) applies an anisotropic smoothing filter, dependent on the direction of the gradient, to the original image to generate an anisotropic blur image. Such is preferable.

Operation and Effect

The above construction also allows provision of the image processing apparatus that eliminates poor visibility in a superimposed portion of the dotted configurations or the two streaks upon removing the false image associated with the statistical noise. The above construction allows the isotropic blurring device and the anisotropic blurring device to generate the blur image directly by bypassing the band image. This achieves an enhanced image processing speed.

With the aspect of the image processing apparatus, it is more preferable that the image processing apparatus performs image processing such that the anisotropic blur image is subtracted from the band image more largely than the isotropic blur image as the edge reliability corresponding to the pixel to be processed becomes higher and the pixel is located in a line figure in the band image.

Operation and Effect

The above construction is a more detailed construction of the image processing apparatus according to the present invention. The image processing is performed to a portion with a high edge reliability such that the anisotropic blur image is subtracted from the band image more largely than the isotropic blur image. This allows output of the processed image with high visibility with no blurred line figure in the band image.

Moreover, in the image processing apparatus, it is more preferable that image processing is performed such that the isotropic blur image and the anisotropic blur image are subtracted less largely from the band image as the edge reliability corresponding to the pixel to be processed becomes lower and the pixel is not located in the linear image in the band image.

Operation and Effect

The above construction is a more detailed construction of the image processing apparatus according to the present invention. When the image processing is performed to the portion with the lower edge reliability so as to suppress subtraction of the blur image, the processed image with high visibility can be outputted without superimposing a new false image derived from the blur image on the band image.

Moreover, it is preferable that the image processing apparatus performs the image processing such that the isotropic blur image is subtracted from the band image more largely than the anisotropic blur image when the edge reliability corresponding to the pixel to be processed represents an intermediate value.

Operation and Effect

The above construction is a more detailed construction of the image processing apparatus according to the present invention. The image processing is performed to a portion with the edge reliability of the intermediate value such that the isotropic blur image is subtracted from the band image more largely than the anisotropic blur image. This allows output of the processed image having high visibility without the random intersection of the dotted configuration of the subject or the contours of the configuration appearing in the band image.

Moreover, it is more preferable that the processed image generating device of the image processing apparatus changes a weighting mode in accordance with frequency components of the band image.

Operation and Effect

The above construction is a more detailed construction of the image processing apparatus according to the present invention. The processed image generating device changes the weighting mode in accordance with the frequency components of the band image, achieving suitable removal of the false image in accordance with the frequency components.

Moreover, it is more preferable that the processed image generating device of the image processing apparatus changes the weighting mode in accordance with information representing an amount of exposure of the original image upon radiography.

Operation and Effect

The above construction is a more detailed construction of the image processing apparatus according to the present invention. The processed image generating device changes the weighting mode in accordance with the information representing an amount of exposure, achieving suitable removal of the false image in accordance with the amount of exposure.

Moreover, it is preferable in the image processing apparatus that the isotropic blurring device changes a shape or a size of the isotropic smoothing filter in accordance with the information representing an amount of exposure of the original image upon radiography or that the anisotropic blurring device changes a shape or a size of the anisotropic smoothing filter in accordance with the information representing an amount of exposure of the original image upon radiography.

Operation and Effect

The above construction is a more detailed construction of the image processing apparatus according to the present invention. The isotropic blurring device changes the shape or the size of the isotropic smoothing filter in accordance with the information representing an amount of exposure, or the anisotropic blurring device changes the shape or the size of the anisotropic smoothing filter in accordance with the information representing an amount of exposure. This causes suitable removal of the false image in accordance with the amount of exposure.

Moreover, it is more preferable that a radiographic apparatus installing the image processing apparatus includes a radiation source configured to emit radiation; a radiation source controller configured to control the radiation source; a detecting device configured to detect the emitted radiation to output detection signals; and an image generating device configured to generate the original image in accordance with the detection signals outputted by the detecting device.

Operation and Effect

The above construction is incorporation of the image processing apparatus of the present invention into an actual radiographic apparatus. When the subject is exposed to a suppressed dose of radiation during fluoroscopy, a false image derived from statistical noise is likely to appear in an obtained image. The image processing apparatus of the present invention removes the false image. Consequently, the radiographic apparatus can be provided that allows output of an image with high visibility even though the radiography is not conducted again or radiography is not conducted with a high dose of radiation for avoiding the false image.

Advantageous Effects of Invention

The present invention allows provision of a high-speed image processing apparatus capable of outputting a processed image of high visibility in accordance with a shape of a configuration of a subject appearing in an original image upon removing a false image associated with statistical noise. Specifically, the image processing apparatus of the present invention generates an isotropic blur image and an anisotropic blur image from the original image. The processed image generating device of the present invention performs image processing by superimposing a band image, the isotropic blur image, and the anisotropic blur image while changing weighting for each pixel in accordance with the edge reliability. For instance, a portion corresponding to the dotted figure in the anisotropic blur image is drawn in a given direction, whereby the figure in the portion is unnatural. On the other hand, a portion corresponding to the intersection is unnatural since the thick-line figure is extremely enhanced. With the aspect of the present invention, such the portions are not used upon generating the band image noise extract. Accordingly, the dotted configuration of the subject or the intersection with the superimposed contours of the configuration in the finally-obtained processed image is not random, and thus holds visibility. As noted above, the processed image can be outputted having high visibility in accordance with a shape of the configuration of the subject appearing in the original image.

Moreover, with the aspect of the present invention, there is only need to hold one of the anisotropic filters for each direction, causing a downsized memory device for storing the anisotropic filters. Furthermore, it may be determined which anisotropic filter is to be used in accordance with the direction of the gradient depending on a portion of the image. This allows provision of the image processing apparatus with an enhanced processing speed.

BRIEF DESCRIPTION OF DRAWINGS

FIGS. 6 and 7 are schematic views each illustrating gradient according to Embodiment 1.

FIGS. 9 to 17 are schematic views each illustrating the image processing apparatus according to Embodiment 1.

FIGS. 20 and 21 are schematic views each illustrating a problem with a conventional apparatus.

DESCRIPTION OF EMBODIMENTS

Now, description will be given hereinunder of concrete examples as an embodiment for carrying out the present invention.

Embodiment 1

One embodiment of the present invention is to be described as under. X-rays in the embodiment correspond to radiation in the present invention. An FPD is the abbreviation of a flat panel detector.

Figure 1:
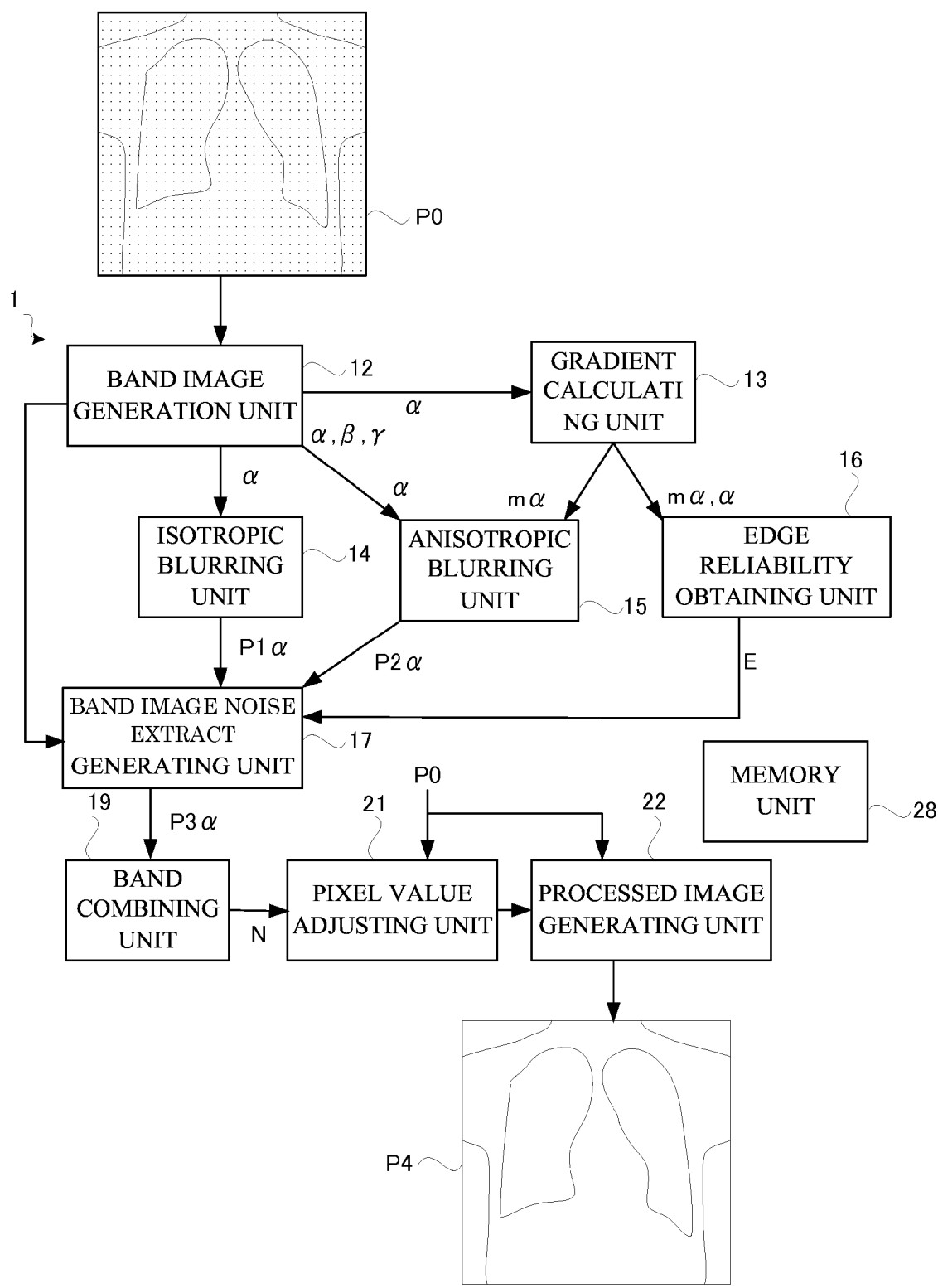
FIG. 1 is a function block diagram illustrating an image processing apparatus according to Embodiment 1.

As illustrated in FIG. 1, in an image processing apparatus 1 according to Embodiment 1, an image (referred to as an original image P0) obtained by fluoroscopying a subject with X-rays is inputted, and then a processed image P4 is outputted. The processed image P4 is obtained by removing a granular false image, derived from statistical noise, that entirely appears in the original image P0. The statistical noise is derived from unevenness of intensity when a detection pixel of the FPD configured to detect X-rays upon fluoroscopy detects X-rays. Thus, the statistical noise has a relationship with a detecting property of a detecting element. Consequently, the granular false image derived from the statistical noise never disappears even when X-rays are uniformly applied to the FPD.

<Whole Construction of Image Processing Apparatus>

The image processing apparatus 1 according to Embodiment 1 includes (A) a band image generating unit 12 configured to generate band images $\alpha, \beta, \gamma \ldots$ with a frequency component of each band being extracted from an original image P0; (B) a gradient calculating unit 13 configured to calculate gradient $m(\alpha, \beta, \gamma \ldots)$ for each of the band images $\alpha, \beta, \gamma \ldots$; (C) an isotropic blurring unit 14 configured to generate isotropic blur images $P1(\alpha, \beta, \gamma \ldots)$ for the band images $\alpha, \beta, \gamma \ldots$, respectively; (D) an anisotropic blurring unit 15 configured to generate anisotropic blur images $P2(\alpha, \beta, \gamma \ldots)$ for the band images $\alpha, \beta, \gamma \ldots$, respectively, with reference to the gradient $m(\alpha, \beta, \gamma \ldots)$; (E) an edge reliability obtaining unit 16 configured to obtain an edge reliability E in accordance with the gradient $m(\alpha, \beta, \gamma \ldots)$; (F) and a band image noise extract generating unit 17 configured to superimpose the band images $\alpha, \beta, \gamma \ldots$, the isotropic blur images $P1(\alpha, \beta, \gamma \ldots)$ and the anisotropic blur images $P2(\alpha, \beta, \gamma \ldots)$, respectively, in accordance with edge reliability E, thereby generating band image noise extracts $P3(\alpha, \beta, \gamma \ldots)$. The gradient calculating unit 13 corresponds to the gradient calculating device in the present invention.

The band image generating unit 12 corresponds to the band image generating device in the present invention. The gradient calculating unit 13 corresponds to the gradient calculating device in the present invention. The isotropic blurring unit 14 corresponds to the isotropic blurring device in the present invention. The anisotropic blurring unit 15 corresponds to the anisotropic blurring device in the present invention. The edge reliability obtaining unit 16 corresponds to the edge reliability obtaining device in the present invention. The band image noise extract generating unit 17 and the processed image generating unit 22 correspond to the processed image generating device in the present invention.

The image processing apparatus 1 further includes a band combining unit 19 configured to superimpose the band image noise extracts $P3(\alpha, \beta, \gamma \ldots)$ to generate a noise image N, a pixel value adjusting unit 21 configured to adjust a pixel value of the noise image N with reference to the original image P0, and a processed image generating unit 22 configured to superimpose the noise image N with the adjusted pixel value on the original image P0 to generate a processed image P4.

Figure 2:
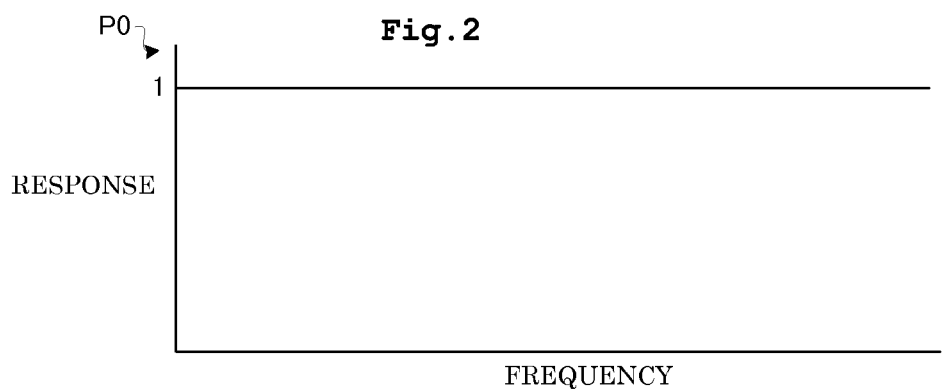
FIGS. 2 to 5 are schematic views each illustrating a band image according to Embodiment 1.
Figure 3:
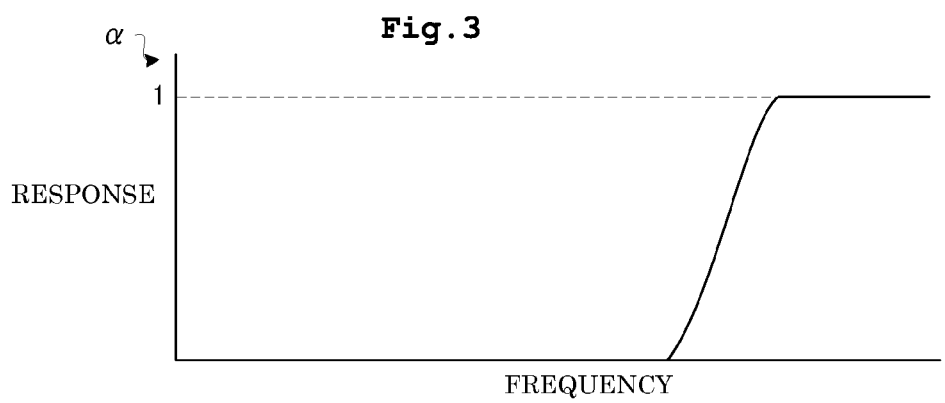
Figure 4:
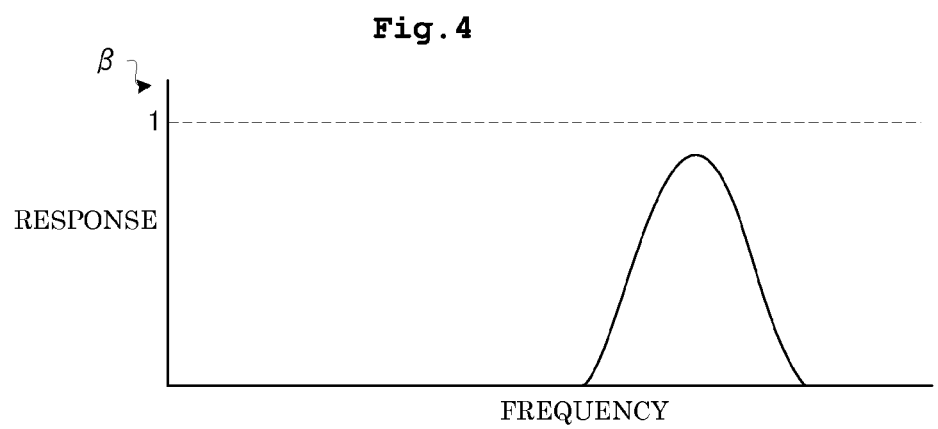
Figure 5:
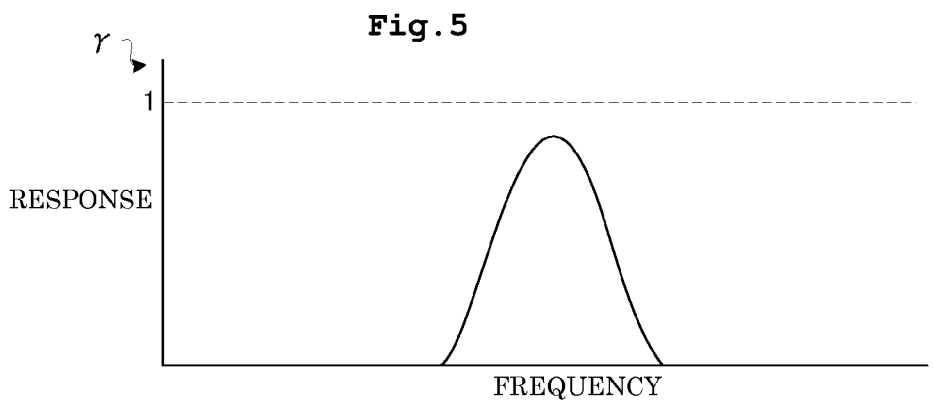

Description will be given of the band images $\alpha, \beta, \gamma \ldots$ generated by the band image generating unit 12. FIG. 2 illustrates a result of performing frequency analysis to the original image P0. The original image P0 has wide frequency components from high frequencies to low frequencies. For expediency of explanation, response of each frequency is assumed 1. FIG. 3 is a result of performing frequency analysis to a band image $\alpha$. As illustrated in FIG. 3, the band image $\alpha$ is obtained by extracting the frequency components within a highest-frequency area of the original image P0. FIG. 4 is a result of performing frequency analysis to a band image $\beta$. As illustrated in FIG. 4, the band image β is obtained by extracting the frequency components within a secondary highest-frequency area of the original image P0. FIG. 5 is a result of performing frequency analysis to a band image γ. As illustrated in FIG. 5, the band image γ is obtained by extracting the frequency components within a thirdly highest-frequency area of the original image P0. As noted above, the band images α, β, γ each have frequency components derived from the original image P0 with frequencies higher in this order. For expediency of explanation, the original image P0 is divided into three band images α, β, γ in this embodiment. However, in actual, three or more band images are generated from the original image P0.

The gradient m represent variations in a pixel value in the band image, and is a data set in which data as characteristic values each corresponding to the pixel of the band image is arranged two-dimensionally. The data constituting the gradient m is in a vector form. The vector has a length corresponding to a value that represents a difference between a value of a pixel in the band image and a pixel therearound. In addition, the vector has a direction where one of the surrounding pixels with the most different value from the center pixel in the band image is located from the center pixel. For instance, in the band image with all the same pixel value, the pixel has the same value as that adjacent to the pixel. Accordingly, the gradient m relative to the band image is filled with data representing 0. That is, the data has neither direction nor length.

On the other hand, FIG. 6 illustrates in the lower side thereof gradient m corresponding to the band image in the upper side thereof, the band image having a portion with different pixel values in the center thereof. Specifically, as is apparent from the lower side of FIG. 6, the gradient m has vectors of data with a longer length at a portion corresponding to a ring-shaped transition of the pixel values in the band image in the upper side of FIG. 6. The length represents the maximum difference of the pixel value between the pixel and the pixel therearound in the band image. In addition, the direction of the vector represents characteristic of the pixel in the band image corresponding to a position of the vector starting point. Specifically, the direction of the vector indicates a direction where the pixel value sharply changes from the pixel to the pixel adjacent thereto. As noted above, the vectors appear in the gradient m along a contour of the subject figure in the band image. The direction where the vector extends is orthogonal to the direction where the contour of the subject figure extends.

All the vectors appearing in the gradient m do not always express the contour of the subject figure. FIG. 7 illustrates on the upper side thereof a band image with a granular false image appearing therein. The false image is derived from the statistical noise. Here, gradient m corresponding to the band image has short vectors, derived from the granular false images, being arranged as illustrated on the lower side of FIG. 7. These vectors do not represent the contour of the subject figure.

As noted above, the actual gradient m is a mix of the vectors representing the contour of the subject figure and the vectors representing the granular false image.

Description will be given of the edge reliability E obtained by the edge reliability obtaining unit 16. The edge reliability E is a value with which it is determined whether each vector in the gradient m represents the contour of the subject figure or the granular false image. Accordingly, the edge reliability exists for each of the vectors in the gradient m, and thus is a characteristic value corresponding to each pixel in the band image. The higher edge reliability E represents a higher possibility that the vectors represent the contour of the subject figure.

The image processing apparatus 1 is provided with a CPU as a hardware source. The CPU executes various programs to provide each unit 11, 12, 13, 14, 15, 16, 17, 18, 19, 21, 22. In addition, the each unit may be divided into arithmetic units which perform their functions. A memory unit 28 stores various parameters, tables, and equations used for image processing. In addition, the memory unit 28 may also store a specification by a user for the image processing in advance.

<Operation of Image Processing Apparatus>

Figure 8:
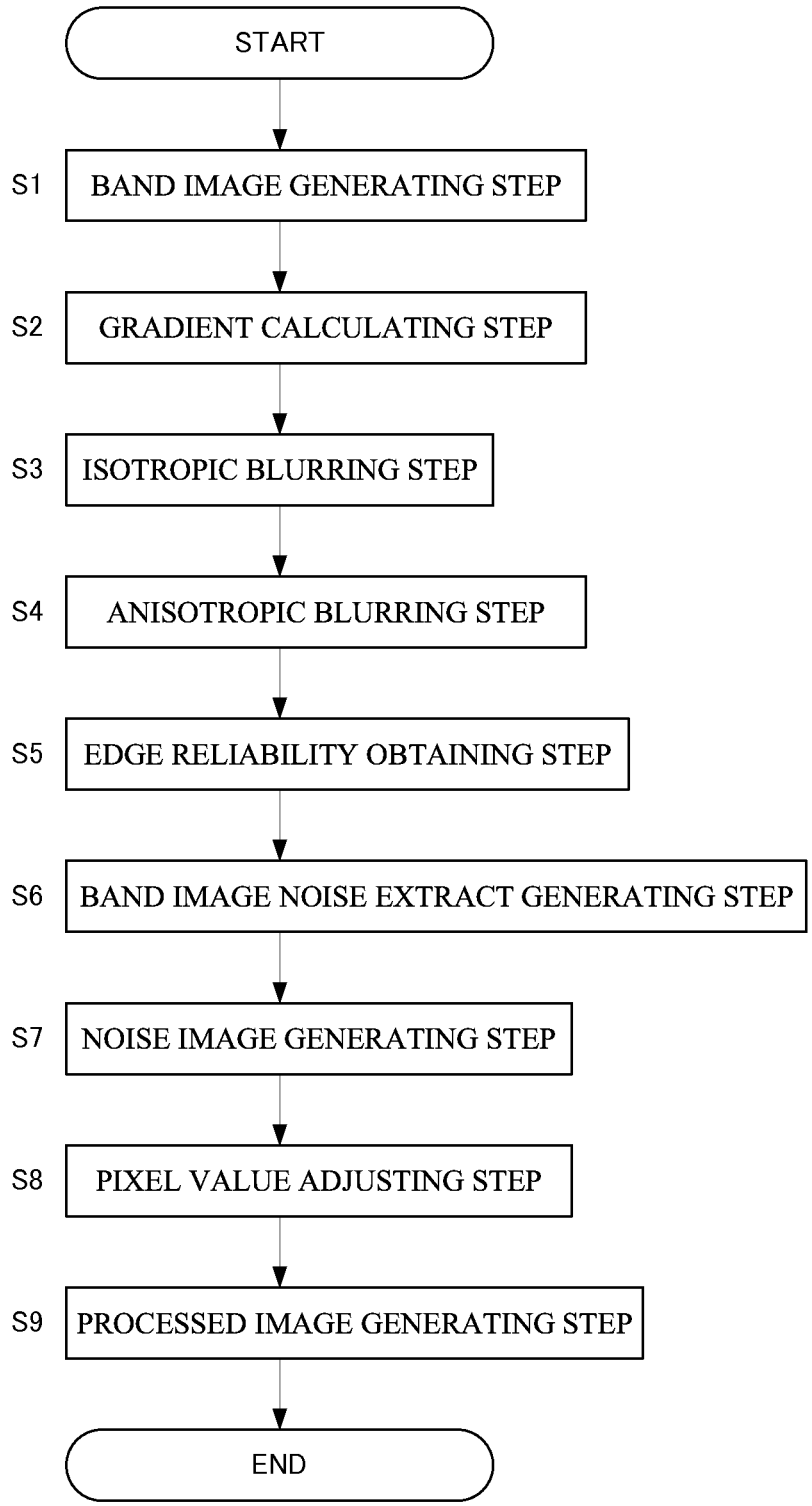
FIG. 8 is a flow chart illustrating an image processing apparatus according to Embodiment 1.

Description will be given next of operation of the image processing apparatus 1. In order to generate a processed image P4 with the image processing apparatus 1 according to Embodiment 1, band images are firstly generated (a band image generating step S1), and gradient m for each of the generated band images is calculated (a gradient calculating step S2), as illustrated in FIG. 8. Thereafter, each of the band images is blurred isotropically to generate an isotropic blur image P1 (an isotropic blurring step S3), and each of the band images is blurred with an anisotropic filter in accordance with the gradient m to generate an anisotropic blur image P2 (an anisotropic blurring step S4). Then, an edge reliability E is obtained in accordance with the gradient m (edge reliability obtaining step S5), and a band image noise extract P3 is generated based on the band image, the isotropic blur image P1, the anisotropic blur image P2, and the edge reliability E (band image noise extract generating step S6). Then, the band image noise extracts P3 are combined to generate a noise image N (noise image generating step S7), and a pixel value of the noise image N is adjusted with reference to the original image P0 (pixel value adjusting step S8), and thereafter the adjusted noise image N is superimposed on the original image P0 to generate a processed image P4 (processed image generating step S9). Hereinunder is description of these steps in order.

<Band Image Generating Step S1>

Figure 9:
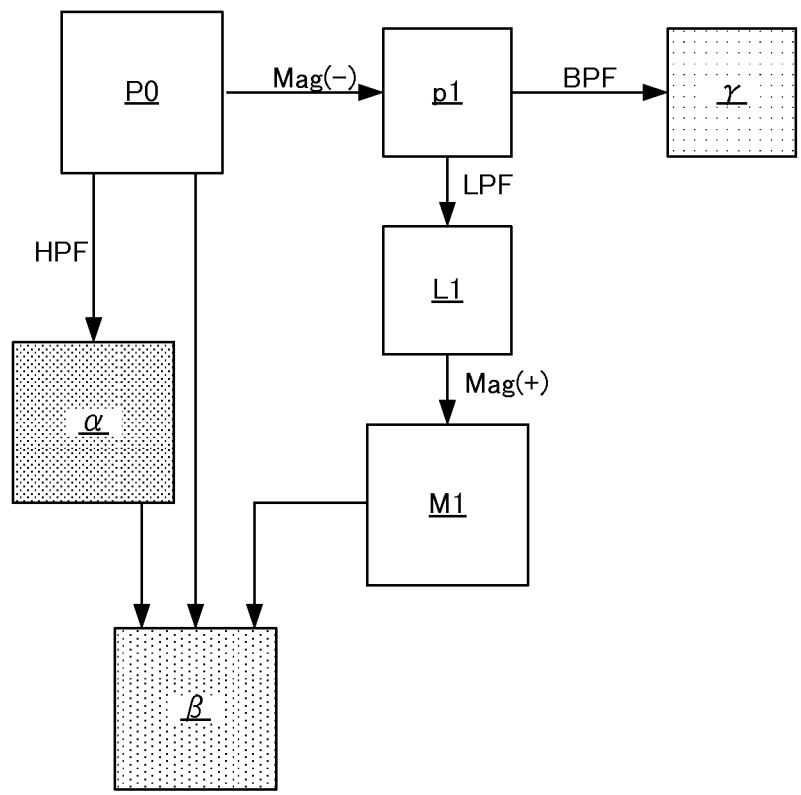

Description will be given of operation of the band image generating unit 12. As illustrated in FIG. 9, the band image generating unit 12 obtains a band image α, a band image β, and a band image γ in this order. Operation for each image is to be described in order. A method of generating the band images α, β, γ as follows is improvement of the conventional Laplacian pyramid decomposition.

Figure 10:
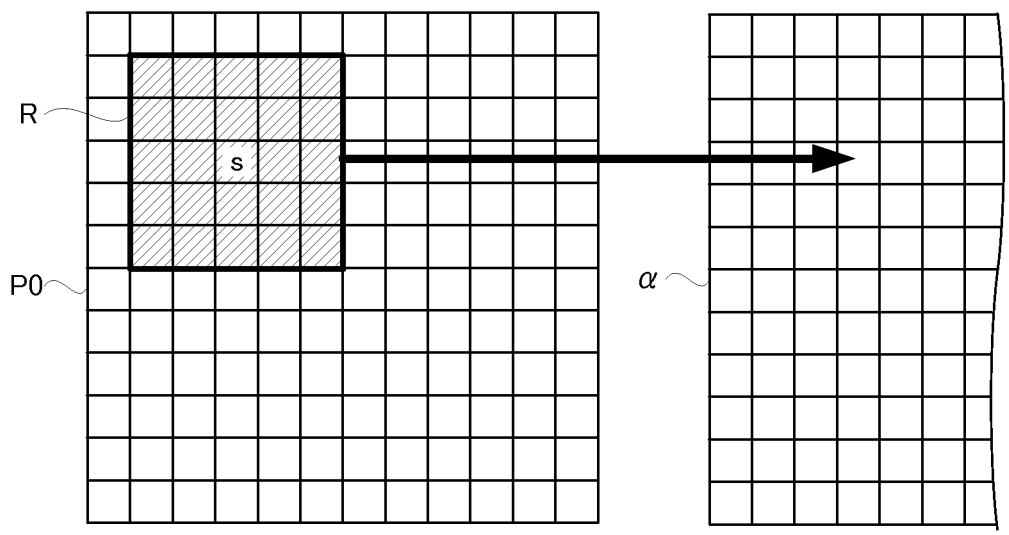

Firstly, description will be given of obtaining the band image α. The original image P0 is sent to the band image generating unit 12. The band image generating unit 12 applies a matrix to each of the pixels constituting the original image P0. The matrix functions as a high-pass filer. FIG. 10 illustrates a state where a pixel s forming the source image P0 is subjected to high-pass filter processing. The band image generation unit 12 reads a matrix of 5 by 5, for example, for the high-pass filter from the memory unit 28, and applies the matrix to the pixel s. Accordingly, as illustrated in FIG. 10, the matrix is applied to a pixel region R of five rows and five columns having the pixel s as a center thereof. Thereafter, the band image generation unit 12 applies pixel data obtained through application of the matrix to a position corresponding to the pixel s (a position same as that of the pixel s) in the band image α. The band image generation unit 12 performs the same operation as above to all pixels, other than the pixel s, that form the source image P0. The acquired pixel data is brought into correspondence with the source image P0, and is mapped in the band image α on each occasion. The high-pass filter transmits only the high-frequency components contained in the pixel region R. Consequently, the first band image α becomes a rough image having the pixel data thereof varying finely. The high-pass filter processing is denoted by a symbol HPF in FIG. 9.

Description will be given next of obtaining the band image β. As illustrated in FIG. 9, the band image generation unit 12 generates a reduction image p1 by reducing the original image P0 by half vertically and horizontally. In FIG. 9, the image-reducing process is denoted by a symbol Mag (−).

Then the band image generating unit 12 performs low-pass filter processing to the reduced image p1. That is, the band image generation unit 12 reads a matrix for the low-pass filter of 5 by 5 from the memory unit 28, the matrix having the same dimension as the matrix for the high-pass filters, and applies the matrix to each of the pixels forming the reduction image p1. The pixel data obtained through application of the matrix is brought into correspondence with the reduction image p1 and is mapped in the low-pass image L1. The situation above is similar to the explanation using FIG. 10. Differences therebetween are the matrix to be used and the reduced size of the image. As noted above, frequency components may be extracted through reducing once the source image P0 and applying the low-pass filter although the matrix specifying the band-pass filter does not increase in dimension. Consequently, a calculation cost may significantly be suppressed. The low-pass filter processing is denoted by a symbol LPF in FIG. 9.

As illustrated in FIG. 9, the band image generation unit 12 generates a magnified image M1 by magnifying the low-pass image L1 twice vertically and horizontally. In FIG. 9, the image-reducing process is denoted by a symbol Mag (+). That is, the magnified low-pass image M1 has the same size as the original image P0. The band image generation unit 12 generates the band image β through subtraction of the band image α and the magnified low-pass image M1 from the original image P0.

Figure 11:
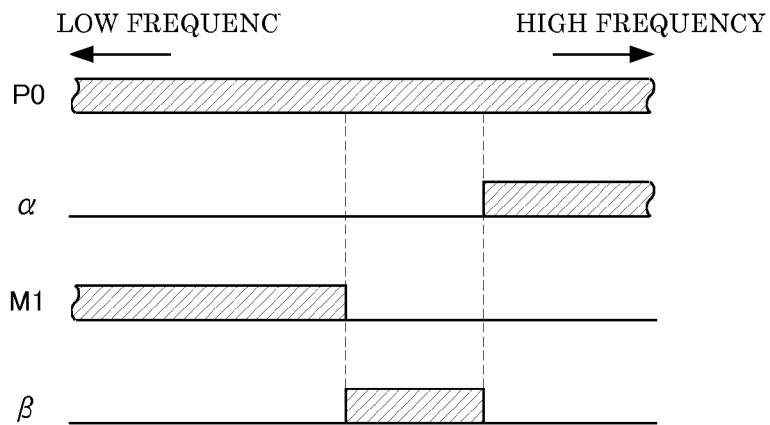

Description will be given of the band image β. FIG. 11 is a schematic view illustrating a range of the frequency components contained in each image. As shown in FIG. 11, the source image P0 entirely has the frequency components. The band image α is formed of only the high-frequency components, whereas the magnified low-pass image M1 is formed of only the low-frequency components of the reduction image p1. As illustrated in FIG. 11, the band image β having the band image α and the magnified low-pass image M1 subtracted from the original image P0 has frequency components among all frequency components of the original image P0 in a range between the lowest-frequency of the band image α and the highest-frequency of the magnified low-pass image M1.

Description will be given next of the band image γ. The band image generation unit 12 reads a matrix for the band-pass filter of 9 by 9 from the memory unit 28 that is approximately twice the matrix for the low-pass filter, and applies the matrix to each of the pixels forming the reduction image p1. The pixel data obtained through application of the matrix is brought into correspondence with the reduction image p1, and is mapped in the third band image β. The situation above is similar to the explanation using FIG. 10. Differences therebetween are various types of matrix to be used, the matrix having appropriately twice the length and width, and the reduction image p1 to be processed having approximately ¼ times the area of the source image P0. In FIG. 9, the band-pass filter processing is denoted by a symbol BPF. The band image γ generated as above additionally has extracted frequency components of the original image P0 in the lower frequency band than the band image β.

The band image generation unit 12 also generates a reduction image p2, in addition to the reduction image P1, that is obtained through reduction of the reduction image p1 by half vertically and horizontally. The reduction image p2 is also subjected to the band-pass filter processing, whereby a band image δ is generated. The band image δ generated as above has extracted frequency components of the original image P0 in the further lower frequency band than the band image γ. In this way, the band image generation unit 12 may generate the band image having the lower frequencies than the band image γ. The band images may also be used in the subsequent image processing. However, image processing is to be performed with the band images α, β, γ only for simple explanation of Embodiment 1.

<Gradient Calculating Step S2>

Figure 12:
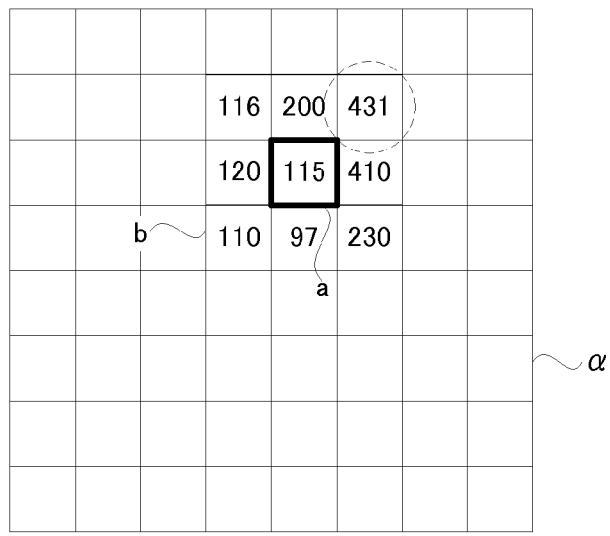
Figure 13:
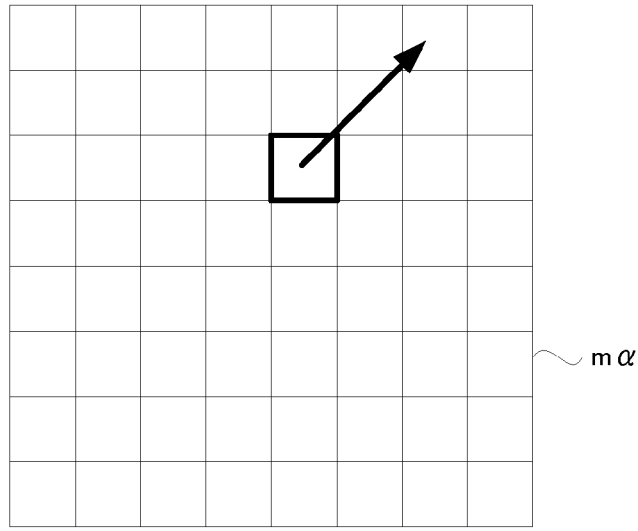

The band images α, β, γ are sent to the gradient calculating unit 13. The gradient calculating unit 13 generates gradient m(α, β, γ) by performing given operation to the band images α, β, γ. FIGS. 12 and 13 each illustrate generation of gradient mα in accordance with the band image a by the gradient calculating unit 13. The gradient calculating unit 13 reads out a pixel value of a target pixel a (target pixel value) constituting the band image α. FIG. 12 includes a pixel value of 115. Then, pixel values of eight surrounding pixels b around the target pixel a (surrounding pixel values) are read out. The pixel values are various as illustrated in FIG. 12. The gradient calculating unit 13 compares the values of the eight surrounding pixels, and selects one pixel b from the eight surrounding pixel values. The pixel b has a pixel value with the most difference (difference of the pixel value) from the target pixel value. In FIG. 12, the selected pixel b is indicated enclosed with dotted lines.

Then, the gradient calculating unit 13 arranges a vector in a position corresponding to the target pixel a in the gradient mα (a position same as that of the target pixel a). The vector has a length representing the pixel value difference of the selected pixel. In addition, the vector has a direction representing a direction of the selected pixel when seen from the target pixel a. The gradient calculating unit 13 calculates the gradient mα for the entire band image α while changing the target pixel a. The gradient calculating unit 13 operates to the other band images in the same manner. As noted above, the gradient calculating unit 13 calculates the magnitude and the direction of the gradient of the pixel value for each pixel of the band images α, β, γ.

<Isotropic Blurring Step S3>

The band images α, β, γ are also sent to the isotropic blurring unit 14. The isotropic blurring unit 14 applies a Gaussian filter to each of the band images α, β, γ to generate isotropic blur images P1(α, β, γ). The isotropic blurring unit 14 applies a matrix specifying the Gaussian filter while changing a target pixel to obtain a value. The values are arranged two-dimensionally to generate an image. The isotropic blurring unit 14 blurs the configuration of the subject and the granular false image derived from the statistical noise. The isotropic blurring unit 14 operates to the other band images in the same manner.

Here, the shape or the magnitude of the Gaussian filter may be changed in accordance with information expressing an amount of exposure upon radiography. Specifically, when the shape or the magnitude of the Gaussian filter is made lower in advance, the noise is made less as a dose of radiation increases. With a reflection of this, the less-blurred isotropic blur images P1(α, β, γ) are obtainable.

<Anisotropic Blurring Step S4>

The gradient m (α, β, γ) is sent to the anisotropic blurring unit 15. The anisotropic blur unit 15 applies an anisotropic blurring filter as in FIG. 14 to the band images α, β, γ, thereby generating anisotropic blur images P2 (α, β, γ). Application of the anisotropic blurring filter to one pixel in the image achieves a blurring effect to the pixel so as to be drawn toward opposite directions. The anisotropic blurring unit 15 performs such blurring to the band image a to generate an anisotropic blur image P2α.

Description will be given of the anisotropic blurring filter. When the anisotropic blurring filter is applied vertically to an image as illustrated in FIG. 15 with a figure appearing in the center thereof, the figure in a circular shape is blurred vertically and drawn as illustrated on the left of FIG. 16. Here, FIG. 16 illustrates a case on the right thereof where an isotropic filter is applied to the image of FIG. 15. When the isotropic filter is applied to the image, the figure in the image is blurred so as to be drawn as it is.

The anisotropic blurring filter is applied to each pixel for generating the anisotropic blur image P2α with the anisotropic blurring unit 15. An application direction of the anisotropic blurring filter varies in accordance with the pixels. Specifically, the anisotropic blurring unit 15 determines the anisotropic blurring filter with reference to the direction of each data in the gradient mα. When the anisotropic blurring unit 15 applies the anisotropic blurring filter to a pixel of the band image α, the anisotropic blurring filter is applied in a direction orthogonal to a direction of vector data on the gradient mα corresponding to the pixel. The anisotropic blurring unit 15 performs similar operation to the other band images.

As illustrated in FIG. 7, the direction of the vector on the gradient mα is orthogonal to a contour of the subject figure in the band image α. Consequently, the anisotropic blurring filter is to be applied along the contour of the subject figure in the band image α as illustrated by solid line arrows on the left of FIG. 17. Accordingly, no subject image becomes blurred upon application of the anisotropic blurring filter. On the other hand, the granular false image superimposed on the contour of the subject figure is blurred and thus becomes invisible.

Moreover, the shape or the magnitude of the anisotropic blurring filter is variable in accordance with the information representing an amount of exposure upon radiography. That is, when the shape or the magnitude of the anisotropic blurring filter is set in advance to be smaller, the noise is less as a dose of radiation increases. With a reflection of this, less-blurred anisotropic blur images P2(α, β, γ) are to be obtained.

From the above description, it is likely to enhance visibility of the anisotropic blur image P2α. However, the anisotropic blurring filter also acts on a portion other than the contour of the subject figure as illustrated by the dotted line arrows on the left of FIG. 17. Consequently, at this portion, slight directionality of the pixel value in the band image α is enhanced, leading to an image with a fluffing object as illustrated on the right of FIG. 17.

<Edge Reliability Obtaining Step S5>

The gradient m(α, β, γ) is also sent to the edge reliability obtaining unit 16. The edge reliability obtaining unit 16 obtains edge reliability E for each data from data on the gradient m(α, β, γ) and data adjacent to the data in the band image, the edge reliability E being an index representing whether or not a difference between the pixel values of the data is derived from noise. Specifically, the edge reliability obtaining unit 16 reads out a vector length (target vector length Vt) of target data constituting the gradient m. Subsequently, each pixel value for eight pieces of surrounding data around the target data in the band image is read out to calculate a difference in pixel value between the target data and the surrounding data, whereby each vector length of the eight pieces of surrounding data (surrounding vector length Vn) is read out. The edge reliability obtaining unit 16 obtains the edge reliability E from the each value in accordance with a following equation. The edge reliability E corresponds to the index in the present invention.

$E = Vt/\text{an average of } Vn$

That is, the edge reliability E is an index representing how the target vector is longer than the vector around the target. If the band image has a portion corresponding to the target vector where only the granular false image with no directionality appears, merely low edge reliability E is obtainable. This is because the surrounding vectors are also long although the target vector is long.

In contrast to this, if the band image has a portion corresponding to the target vector where a contour of the subject appears, the portion has directionality. That is, the target vector on the contour of the subject is noticeably longer than the surrounding vectors. As a result, high edge reliability E is obtainable to such the target vector.

In addition, an intersection of the contours of the subject in the band image is defined in a direction where the target vector is orthogonal to the thick-line figure, and the length of the vector is also controlled. Consequently, the edge reliability E at the intersection has an intermediate value. The portions in the anisotropic blur images P2(α, β, γ) each have low visibility since the thick-line figure is extremely enhanced.

On the other hand, in the portion of the band image where a dotted configuration of the subject exists, the target vector is defined in a given direction, and an average of the lengths of the surrounding vectors becomes large. Consequently, edge reliability E in the dotted configuration has an intermediate value. The portions in the anisotropic blur images P2(α, β, γ) each have low visibility since the dotted object is drawn in a given direction.

The edge reliability obtaining unit 16 calculates the edge reliability E for the gradient m(α, β, γ) individually. When the gradient mα has pixels of 1,000×1,000 vertically and horizontally, the edge reliability E is to be calculated 2,250,000 times for three types of gradient m(α, β, γ).

<Band Image Noise Extract Generating Step S6>

The edge reliability E is sent to the band image noise extract generating unit 17. The band image noise extract generating unit 17 superimposes the band images α, β, γ, the isotropic blur images P1(α, β, γ), and the anisotropic blur images P2(α, β, γ), respectively, while changing weighting for every pixel, thereby generating images of band image noise extracts P3(α, β, γ) with only the noise components being extracted from the band images α, β, γ.

The band image noise extract generating unit 17 subtracts components other than the noise components from the band images α, β, γ, thereby extracting the noise components from the band images α, β, γ. At this time, the band image noise extract generating unit 17 weights the values of the three pixels located in the same position in the band images α, β, γ, the isotropic blur image P1(α, β, γ), and the anisotropic blur image P2(α, β, γ), respectively, while superimposes the images, thereby obtaining new pixel values. In other words, the band image noise extract generating unit 17 obtains the new pixel values while shifting positions of the pixels in the band images α, β, γ. The obtained pixel values are arranged two-dimensionally in the same manner in the band images α, β, γ to generate band image noise extracts P3(α, β, γ), respectively. That is, the band images α, β, γ, the isotropic blur images P1(α, β, γ), and the anisotropic blur images P2(α, β, γ) are combined into one image. The band image noise extracts P3(α, β, γ) generated at this time are each an image from which only noises are extracted from the band images α, β, γ. Description will be given hereinafter of a method of generating the band image noise extract P3α for the band image α. Similar operation as above is performed to the other band images β, γ are to generate band image noise extracts P3(β, γ), respectively.

Description will be given of a detailed construction when the band image noise extract generating unit 17 performs image processing to the pixel to be processed (target pixel). The band image noise extract generating unit 17 performs different operations to obtain a new pixel value from the values of the three target pixels in accordance with the edge reliability E corresponding to the target value. Here, the three target pixels are located in the same position in different three types of images (the band image, the isotropic blur image, and the anisotropic blur image). Specifically, when the edge reliability E corresponding to the target pixel is high and this represent the pixel in the line object appearing in the band image α, the band image noise extract generating unit 17 subtracts the anisotropic blur image P2α largely than the isotropic blur image P1α from the band image α. Since the contour of the subject appears in the portion, the contour of the subject with the noise being removed therefrom clearly appears in the anisotropic blur image P2α. As a result, when the band image noise extract generating unit 17 subtracts the anisotropic blur image P2α preferentially from the band image α, components of the subject in the band image α are removed and thus the noise components remain.

Moreover, when the edge reliability E corresponding to the target pixel is in an intermediate range, and represents the pixel located at the intersection of the two line objects (profiles of the subjects) appearing in the band image α, the band image noise extract generating unit 17 performs image processing such that the isotropic blur image P1α is subtracted from the band image a more largely than the anisotropic blur image P2α. Since the dotted configuration or the intersection of the contours of the subject appears in the portion, the anisotropic blur image P2α has no suitable visibility. On the other hand, the isotropic blur image P1α has blurred noise components of the band image α and reduced noise components. Consequently, when the band image noise extract generating unit 17 subtracts the isotropic blur image P1α preferentially from the band image α, components of the subject in the band image α are removed and thus the noise components remain.

Moreover, when the edge reliability E corresponding to the target pixel is low and represents the pixel not located in the line object in the band image, the band image noise extract generating unit 17 performs image processing such that the isotropic blur image P1α and the anisotropic blur image P2α are subtracted from the band image α less largely comparing the case when the edge reliability E is high. No subject image appears in the portion and many noise components are contained in the band image α. Accordingly, the noise components can be extracted from the portion without performing subtraction so much from the band image α.

The band image noise extracts P3(α, β, γ) generated by the band image noise extract generating unit 17 in this manner are obtained by extracting the noise components from the band images α, β, γ, respectively.

Description will be given next of a method of identifying the edge reliability E. The band image noise extract generating unit 17 performs identification of whether or not the edge reliability E is high in accordance with tables or equations stored in the memory unit 28. Here, the table is a data set associated with the edge reliability E, a coefficient representing an extent of subtracting the isotropic blur image P1α, and a coefficient representing an extent of subtracting the anisotropic blur image P2α. The band image noise extract generating unit 17 reads out the edge reliability E, corresponding to the target pixel, upon processing the target pixel, thereby obtaining a coefficient corresponding to the edge reliability E from the table. Then the band image noise extract generating unit 17 performs subtraction to the isotropic blur image P1α and the anisotropic blur image P2α relative to the band image a in accordance with the obtained coefficient.

The table may be variable in accordance with bands of the band images α, β, γ. Alternatively, a weighting mode may be variable in accordance with the information representing an amount of exposure upon radiographing the original image P0. The edge reliability E is substituted for the equation used with the band image noise extract generating unit 17 to achieve derivation of each coefficient above.

Specifically, the table is varied so as to have larger values as the band image is of low frequency. In addition, a relationship between the pixel value of the original image P0 and the incidence dose of radiation is determined in advance, and the table is varied so as to have larger values as the pixel value of the original image P0 becomes larger. This obtains less-blurred band image noise extracts P3(α, β, γ) reflecting the property of less noise with low frequency and a large amount of exposure. Instead of the pixel value of the original image P0, the pixel value of the enlarged low-pass image M1 with less noise may be used as an index for an amount of exposure.

<Noise Image Generating Step S7>

The band image noise extracts P3(α, β, γ) are sent to the band combining unit 19. The band combining unit 19 superimposes the band image noise extracts P3(α, β, γ) on one another while applying weight to generate a noise image N. The noise image N represents all frequencies for the original image P0. The weight upon superimposing the band image noise extracts P3(α, β, γ) with the band combining unit 19 is variable depending on inspection purposes.

<Pixel Value Adjusting Step S8>

The noise image N is sent to the pixel value adjusting unit 21. The pixel value adjusting unit 21 adjusts each value of pixels constituting the noise image N with reference to the original image P0. Specifically, the pixel value adjusting unit 21 adjusts a pixel value of the target pixel with reference to the value of the pixel in the original image P0, the pixel corresponding to pixel to be processed (target pixel) in the noise image N. Such adjusting process achieves enhanced visibility of the finally-obtained image. The pixel value adjusting unit 21 adjusts the pixel value variously in accordance with inspection purposes.

<Processed Image Generating Step S9>

The noise image N having the adjusted pixel value is sent to the processed image generating unit 22. The processed image generating unit 22 performs subtraction of the weighted noise image N from the original image P0. Since the noise image N is obtained by extracting the noise components from the original image P0, the noise components in the original image P0 are eliminated by subtracting the noise image N. As noted above, a processed image P4 is generated with suppressed noise components. In addition, in a portion of the original image P0 (correctly, the band images α, β, γ) with the intermediate value of the edge reliability E, an influence of the anisotropic blur image P2α is suppressed to generate the processed image P4. Accordingly, no image is random at the intersection in the processed image P4 where the dotted configuration or the contours of the subject are superimposed. Moreover, adjusting the weighting of the noise image N achieves convenient adjustment of intensity of the process.

The weighting of the noise image N with the processed image generating unit 22 is variable in accordance with the inspection purposes.

As noted above, according to the construction of Embodiment 1, the high-speed image processing apparatus 1 can be provided with which no visibility is increased at the intersection of dotted configuration or two streaks upon removing the false image associated with the statistical noise. Specifically, the image processing apparatus 1 according to Embodiment 1 generates the isotropic blur image P1 and the anisotropic blur image P2 from the original image P0 (correctly, the band images $\alpha$, $\beta$, $\gamma$). The isotropic blur image P1 is an image obtained by suitably removing the false image from a portion of the original image P0 where no subject appears, whereas the anisotropic blur image P2 is an image obtained by suitably removing the false image from a portion where the subject appears. Then, the band image noise extract generating unit 17 superimposes the two images on the band images $\alpha$, $\beta$, $\gamma$ while performing weighting for every pixel, thereby generating the band image noise extract P3 with the false image being extracted from the band images $\alpha$, $\beta$, $\gamma$. The band image noise extract P3 is used for removing the false image appearing in the original image P0.

The most characteristic in the construction according to Embodiment 1 is performance of the image processing such that band image noise extract generating unit 17 subtracts the isotropic blur image P1 from the band images $\alpha$, $\beta$, $\gamma$ more largely than the anisotropic blur image P2 when the edge reliability E corresponding to the target pixel has an intermediate value. Here, the edge reliability E is an index for determination of which the subject image or the false image causes variation in pixel value between the target pixel and the surrounding pixels. When the edge reliability E has an intermediate value, the target pixel is located at the intersection of the dotted configuration or two line objects appearing in the band images $\alpha$, $\beta$, $\gamma$. With the construction according to Embodiment 1, the band image noise extract P3 is generated without using the anisotropic blur image P2 at the intersection (if using, with an intensity lower than that of the isotropic blur image P1). A portion corresponding to the intersection in the anisotropic blur image P2 is unnatural since slight variations in pixel value are extremely enhanced. With the construction according to Embodiment 1, such the portion is not used upon generating the band image noise extract P3. Accordingly, the intersection in the finally-obtained processed image P4 where the contours of the configuration of the subject are superimposed is not random, and thus holds visibility.

Moreover, with the construction of Embodiment 1, there is no need to hold a plurality of anisotropic filters for every direction as in the conventional construction, causing a downsized memory device for storing them. Furthermore, it may be determined which anisotropic filter is to be used in accordance with the direction of the gradient depending on a portion of the image. This allows provision of the image processing apparatus with an enhanced processing speed.

In addition, the image processing is performed to a portion with the high edge reliability E such that the anisotropic blur image P2 is subtracted from the band images $\alpha$, $\beta$, $\gamma$ more largely than the isotropic blur image P1. This allows output of the processed image P4 with high visibility with no blur line object in the band images $\alpha$, $\beta$, $\gamma$.

As noted above, when the image processing is performed to the portion with the lower edge reliability E so as to suppress subtraction of the blur image, the processed image P4 with high visibility can be outputted without superimposing a new false image derived from the blur image on the band images $\alpha$, $\beta$, $\gamma$.

Moreover, the band image noise extract generating unit 17 changes the weighting mode in accordance with the frequency components of the band image, achieving suitable removal of the false image in accordance with the frequency components.

Moreover, the band image noise extract generating unit 17 changes the weighting mode in accordance with the information representing an amount of exposure, achieving suitable removal of the false image in accordance with an amount of exposure.

Moreover, the isotropic blurring unit 14 changes the shape or the magnitude of the Gaussian filter in accordance with the information representing an amount of exposure upon radiography, or the anisotropic blurring unit 15 changes the shape or the magnitude of the anisotropic blurring filter in accordance with the information representing an amount of exposure upon radiography. This causes suitable removal of the false image in accordance with an amount of exposure.

Embodiment 2

Figure 18:
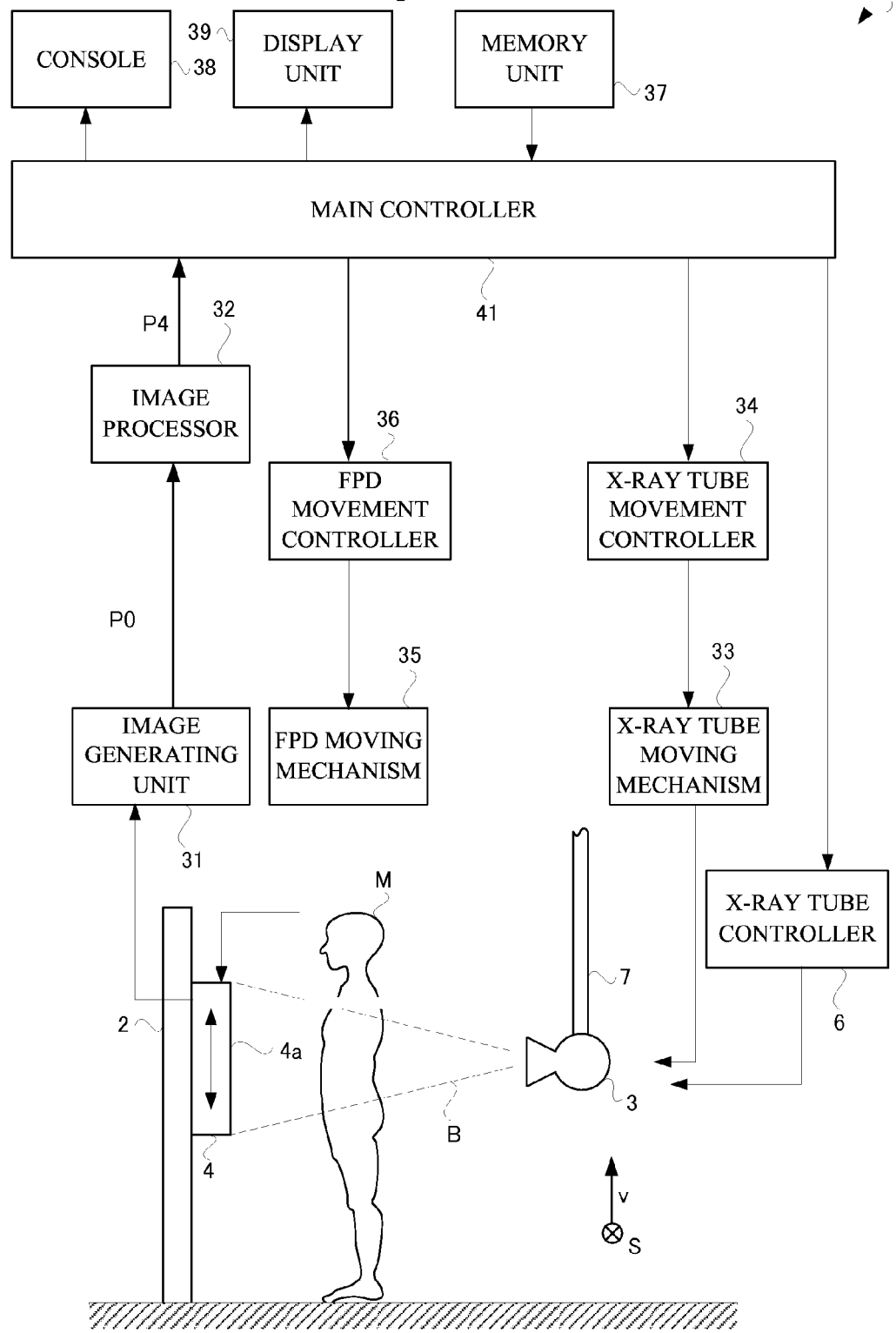
FIG. 18 is a function block diagram illustrating an X-ray apparatus according to Embodiment 2.

Description will be given next of an X-ray apparatus 20 according to Embodiment 2. As illustrated in FIG. 18, the X-ray apparatus 20 according to Embodiment 2 is an X-ray apparatus for radiography in a standing position including the image processing apparatus 1 (in FIG. 18, illustrated as an image processor 32) according to Embodiment 1. Consequently, description about the construction and operation of the image processor 32 according to Embodiment 1 is to be omitted in description of the X-ray apparatus 20 according to Embodiment 2.

Now the construction of the X-ray apparatus 20 according to Embodiment 2 is to be described. The X-ray apparatus 20 performs radiography to a subject M in a standing position. As illustrated in FIG. 18, the X-ray apparatus 20 includes a strut 2 extending in a vertical direction v from the floor, an X-ray tube 3 emitting X-rays, an FPD 4 supported on the strut 2, and a suspending supporter 7 extending in the vertical direction v and supported on the ceiling. The suspending supporter 7 suspendingly supports the X-ray tube 3. The X-ray tube 3 corresponds to a radiation source in the present invention. The FPD 4 corresponds to a detecting device in the present invention.

The FPD 4 is slidable in the vertical direction v relative to the strut 2. The suspending supporter 7 is also expandable in the vertical direction v. A position of the X-ray tube 3 in the vertical direction v is variable with expansion of the suspending supporter 7. An FPD moving mechanism 35 between the above elements 2 and 4 moves the FPD 4 in the vertical direction v relative to the strut 2. An FPD movement controller 36 controls movement of the FPD moving mechanism 35.

Description will be given of movement of the X-ray tube 3. The X-ray tube 3 is moved by an X-ray tube moving mechanism 33 provided in the suspending supporter 7. An X-ray tube movement controller 34 is provided for controlling the X-ray tube moving mechanism 33. The X-ray tube moving mechanism 33 moves the X-ray tube 3 (1) in the vertical direction v, (2) in directions approaching and away from the FPD 4, and (3) in a horizontal direction S orthogonal to a direction from the X-ray tube 3 to the FPD 4 (in FIG. 18, a plane-passing direction, a body-side direction of the subject M). The suspending supporter 7 expands and contracts when the X-ray tube 3 is moved in the vertical direction v.

The FPD 4 has a detecting surface 4a configured to detect X-rays (see FIG. 18). The detecting surface 4a stands erect in the vertical direction v and is provided in the X-ray apparatus 20. This achieves effective radiography to the standing subject M. The detecting surface 4a faces to an X-ray emitting hole of the X-ray tube 3. In other words, the detecting surface 4a is arranged along a plane made by two directions, i.e., the horizontal direction S and the vertical direction v. The detecting surface 4a is rectangular, one side thereof corresponding to the horizontal direction S and the other side orthogonal to the one side corresponding to the vertical direction v.

An X-ray tube controller 6 controls a tube voltage and a tube current of the X-ray tube 3 and an irradiation time of X-rays. The X-ray tube controller 6 controls the X-ray tube 3 with a given tube current, a tube voltage, and a pulse width. Parameters, such as the tube current, are stored in a memory unit 37. The X-ray tube controller 6 corresponds to a radiation source controller in the present invention.

An image generating unit 31 constructs detection data outputted from the FPD 4 to generate an original image P0 with a projection image of the subject M appearing therein. The image processor 32 removes a false image derived from statistical noise appearing in the original image P0, thereby generating a processed image P4. The image generating unit 31 corresponds to an image generating device in the present invention.

A console 38 is provided for inputting operator's instructions. Various commands to the image processor 32 are issued via the console 38. A memory unit 37 stores all the parameters, such as control information of the X-ray tube 3, positional information of the X-ray tube 3, and positional information in the vertical direction v of the FPD 4, that are used for X-ray radiography. Here, as illustrated in FIG. 18, the X-ray apparatus 20 includes a main controller 41 configured to control en bloc each of units 6, 34, 36, 31, 32. The main controller 41 has a CPU, and provides each unit executing various programs. The above units may be divided into arithmetic units that perform their functions. A display unit 39 is provided for displaying the processed image P4 obtained through radiography.

<Operation X-ray Apparatus>

Next, description will be given of operations of the X-ray apparatus 20. Prior to radiography, the subject M stands between the X-ray tube 3 and the FPD 4. Consequently, the subject M is to be placed in the X-ray apparatus 20. When an operator adjusts positions of the X-ray tube 3 and the FPD 4 via the console 38, the X-ray tube 3 and the FPD 4 are moved to an imaging area of the subject M in accordance with control of the controllers 34, 36 configured to control the X-ray tube 3 and the FPD 4, respectively.

When the operator issues a command to start radiography via the console 38, the X-ray tube controller 6 emits pulsed X-rays in accordance with the irradiation time, the tube current, and the tube voltage stored in the memory unit 37. The FPD 4 detects X-rays transmitted through the subject, and outputs detection signals to the image generating unit 31. The image generating unit 31 generates the original image P0 in accordance with each of the detection signals. The original image P0 has a fluoroscopic image of the subject M and a false image derived from the statistical noise appearing therein. The image processor 32 converts the original image P0 into the processed image P4 with the false image removed therefrom. When the processed image P4 is displayed on a display unit 39, radiography with the X-ray apparatus 20 is completed.

As noted above, in Embodiment 2, the image processing apparatus 1 according to Embodiment 1 is incorporated into an actual radiographic apparatus. When exposure to the subject is to be suppressed during fluoroscopy, the false image derived from the statistical noise is likely to appear in the obtained image. The false image is eliminated with the image processing apparatus 1 according to Embodiment 1. Consequently, the radiographic apparatus can be provided that allows output of an image having excellent visibility with no need of radiography at a high dose of radiation for avoiding the false image.

The present invention is not limited to the foregoing configurations, but may be modified as follows.

Figure 19:
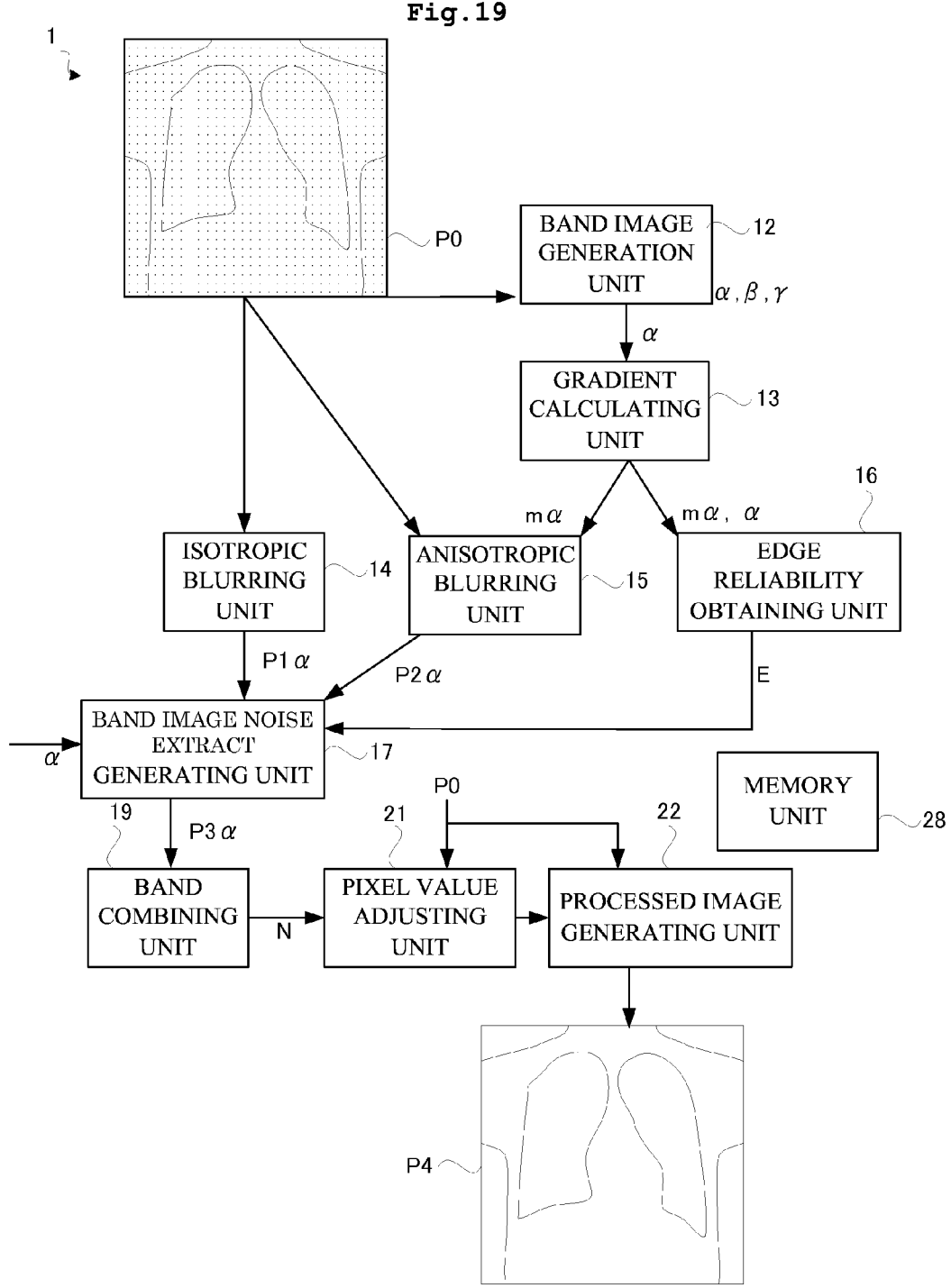
FIG. 19 is a function block diagram illustrating one deformation of the present invention.

(1) With the foregoing embodiments, the band images $\alpha$, $\beta$, $\gamma$ are inputted in the isotropic blurring unit 14 and the anisotropic blurring unit 15. Instead of this, the original image P0 may be inputted as illustrated in FIG. 19. At this time, the units 14, each perform blurring and simultaneously extract a given frequency in the original image P0, which differs from the foregoing embodiments. Accordingly, the isotropic blur images P1 ($\alpha$, $\beta$, $\gamma$) and the anisotropic blur images P2($\alpha$, $\beta$, $\gamma$) can be generated in one step from the original image P0. This achieves provision of an image processing apparatus with a simple construction and high-speed operation.

(2) The foregoing examples discuss a medical apparatus. The present invention is applicable also to an apparatus for industrial use or for the nuclear field.

(3) X-rays used in the foregoing embodiments are an example of radiation in the present invention. Therefore, the present invention may be adapted also to radiation other than X-rays.

INDUSTRIAL APPLICABILITY

As noted above, the image processing apparatus of the present invention is suitable in a medical field.

REFERENCE SIGN LIST

3 X-ray tube (radiation source)
4 FPD (detecting device)
6 X-ray tube controller (radiation source controller)
a target pixel
b surrounding pixel
m gradient
E edge reliability
P0 original image
P1 isotropic blur image
P2 anisotropic blur image
P3 band image noise extract
P4 processed image
$\alpha$, $\beta$, $\gamma$ band image
12 band image generating unit (band image generating device)
13 gradient calculating unit (gradient calculating device)
14 isotropic blurring unit (isotropic blurring device)
15 anisotropic blurring unit (anisotropic blurring device)
16 edge reliability obtaining unit (edge reliability obtaining device)
17 band image noise extract generating unit (processed image generating device)
22 processed image generating unit (processed image generating device)
31 image generating unit (image generating device)

The invention claimed is:

1. An image processing apparatus for processing an image obtained by fluoroscopying a subject, the image processing apparatus includes:
(A) a device configured to generate a band image by extracting a part of frequency components in an original image with a figure of the subject appearing therein;
(B) a device configured to calculate magnitude and a direction of gradient of a pixel value for each pixel of the band image;

(C) an isotropic blurring device configured to generate an isotropic blur image by applying an isotropic smoothing filter to the band image;

(D) an anisotropic blurring device configured to generate an anisotropic blur image by applying an anisotropic smoothing filter to the band image, the anisotropic smoothing filter depending on the direction of the gradient;

(E) a device configured to calculate an index for the each pixel in accordance with the magnitude of the gradient and pixel values surrounding the pixel in the band image; and (F) a processed image generating device configured to superimpose the band image, the isotropic blur image, and the anisotropic blur image for the each pixel with weighting based on the index, thereby generating a processed image with a noise component removed from the original image.

2. An image processing apparatus for processing an image obtained by fluoroscopying a subject, the image processing apparatus includes:

(A) a device configured to generate a band image by extracting a part of frequency components in an original image with a figure of the subject appearing therein;

(B) a device configured to calculate magnitude and a direction of gradient of a pixel value for each pixel of the band image;

an isotropic blurring device;

(c) an isotropic blurring device configured to apply an isotropic smoothing filter to the original image to generate an isotropic blur image;

(d) a device configured to apply an anisotropic smoothing filter, dependent on the direction of the gradient, to the original image to generate an anisotropic blur image;

(E) a device configured to calculate an index for the each pixel in accordance with the magnitude of the gradient and pixel values surrounding the pixel in the band image; and (F) a processed image generating device configured to superimpose the band image, the isotropic blur image, and the anisotropic blur image for the each pixel with weighting based on the index, thereby generating a processed image with a noise component removed from the original image.

3. The image processing apparatus according to claim 1, wherein
the image processing apparatus performs image processing so as the anisotropic blur image to be subtracted from the band image more largely than the isotropic blur image as the edge reliability corresponding to the pixel to be processed becomes higher.

4. The image processing apparatus according to claim 1, wherein
the image processing apparatus performs image processing so as the isotropic blur image and the anisotropic blur image to be subtracted less largely from the band image as the edge reliability corresponding to the pixel to be processed becomes lower.

5. The image processing apparatus according to claim 1, wherein
the image processing apparatus performs image processing so as the isotropic blur image to be subtracted from the band image more largely than the anisotropic blur image when the edge reliability corresponding to the pixel to be processed represents an intermediate value.

6. The image processing apparatus according to claim 1, wherein
the processed image generating device changes a weighting mode in accordance with frequency components of the band image.

7. The image processing apparatus according to claim 1, wherein
the processed image generating device changes the weighting mode in accordance with information representing an amount of exposure of the original image upon radiography.

8. The image processing apparatus according to claim 1, wherein
the isotropic blurring device changes a shape or a size of the isotropic smoothing filter in accordance with the information representing the amount of exposure of the original image upon radiography, or
the anisotropic blurring device changes a shape or a size of the anisotropic smoothing filter in accordance with the information representing the amount of exposure of the original image upon radiography.

9. A radiographic apparatus including the image processing apparatus according to claim 1, the radiographic apparatus including:
a radiation source configured to emit radiation;
a radiation source controller configured to control the radiation source;
a detecting device configured to detect the emitted radiation to output detection signals; and
an image generating device configured to generate the original image in accordance with the detection signals outputted by the detecting device.

10. The image processing apparatus according to claim 2, wherein
the image processing apparatus performs image processing so as the anisotropic blur image to be subtracted from the band image more largely than the isotropic blur image as the edge reliability corresponding to the pixel to be processed becomes higher.

11. The image processing apparatus according to claim 2, wherein
the image processing apparatus performs image processing so as the isotropic blur image and the anisotropic blur image to be subtracted less largely from the band image as the edge reliability corresponding to the pixel to be processed becomes lower.

12. The image processing apparatus according to claim 2, wherein
the image processing apparatus performs image processing so as the isotropic blur image to be subtracted from the band image more largely than the anisotropic blur image when the edge reliability corresponding to the pixel to be processed represents an intermediate value.

13. The image processing apparatus according to claim 2, wherein
the processed image generating device changes a weighting mode in accordance with frequency components of the band image.

14. The image processing apparatus according to claim 2, wherein
the processed image generating device changes the weighting mode in accordance with information representing an amount of exposure of the original image upon radiography.

15. The image processing apparatus according to claim 2, wherein
the isotropic blurring device changes a shape or a size of the isotropic smoothing filter in accordance with the information representing the amount of exposure of the original image upon radiography, or
the anisotropic blurring device changes a shape or a size of the anisotropic smoothing filter in accordance with the information representing the amount of exposure of the original image upon radiography.

16. A radiographic apparatus including the image processing apparatus according to claim 2, the radiographic apparatus including:
a radiation source configured to emit radiation;
a radiation source controller configured to control the radiation source;
a detecting device configured to detect the emitted radiation to output detection signals; and an image generating device configured to generate the original image in accordance with the detection signals outputted by the detecting device.

\* \* \* \* \*